(12) United States Patent
Liu et al.

(10) Patent No.: US 9,173,708 B2
(45) Date of Patent: Nov. 3, 2015

(54) DERMATOLOGICAL TREATMENT DEVICE WITH ONE OR MORE LASER DIODE BAR

(75) Inventors: Harvey I-Heng Liu, Fremont, CA (US); Tobin C. Island, Oakland, CA (US)

(73) Assignee: TRIA BEAUTY, INC., Dublin, CA (US)

( * ) Notice: Subject to any disclaimer, the term of this patent is extended or adjusted under 35 U.S.C. 154(b) by 0 days.

(21) Appl. No.: 13/426,206

(22) Filed: Mar. 21, 2012

(65) Prior Publication Data

US 2012/0253331 A1 Oct. 4, 2012

Related U.S. Application Data

(60) Provisional application No. 61/469,316, filed on Mar. 30, 2011, provisional application No. 61/533,641, filed on Sep. 12, 2011, provisional application No. 61/533,677, filed on Sep. 12, 2011, provisional application No. 61/533,786, filed on Sep. 12, 2011, provisional application No. 61/545,481, filed on Oct. 10, 2011, provisional application No. 61/563,491, filed on Nov. 23, 2011.

(51) Int. Cl.
*A61B 18/18* (2006.01)
*A61B 18/20* (2006.01)

(52) U.S. Cl.
CPC ...................................... *A61B 18/20* (2013.01)

(58) Field of Classification Search
CPC ................ A61N 2005/0644; A61N 2005/067; A61N 5/0616
USPC ...................................................... 606/2–19
See application file for complete search history.

(56) References Cited

U.S. PATENT DOCUMENTS

| | | | |
|---|---|---|---|
| 5,541,949 A | 7/1996 | Bhat et al. | 372/45.011 |
| 7,763,016 B2 | 7/2010 | Altshuler et al. | 606/9 |
| 2004/0152943 A1 | 8/2004 | Zimmerman et al. | 600/13 |
| 2006/0004306 A1* | 1/2006 | Altshuler et al. | 601/3 |
| 2007/0032847 A1 | 2/2007 | Weckwerth et al. | 607/93 |
| 2008/0015556 A1 | 1/2008 | Chan et al. | 606/9 |
| 2008/0058783 A1* | 3/2008 | Altshuler et al. | 606/9 |
| 2008/0077198 A1 | 3/2008 | Webb et al. | 607/88 |

(Continued)

FOREIGN PATENT DOCUMENTS

| | | | | |
|---|---|---|---|---|
| EP | 1146617 A2 | 10/2001 | | A61B 18/20 |
| GB | 2381752 A | 5/2003 | | A61B 18/20 |

OTHER PUBLICATIONS

Paschotta, Rüdiger, "Diode Bars," Encyclopedia of Laser Physics and Technology, RP Photonics Consulting GmbH, www.rp-photonics.com/diode_bars.html, 7 pages, May 27, 2011.

(Continued)

*Primary Examiner* — Aaron Roane
(74) *Attorney, Agent, or Firm* — Slayden Grubert Beard PLLC

(57) ABSTRACT

A dermatological treatment device includes a device body; a laser diode bar configured to generate laser radiation for delivery to a target area of tissue, the laser diode bar having a fill factor of at least 50%; a power source; and control electronics configured to provide power from the power source to the laser diode bar such that the laser diode bar generates a laser beam; wherein the device is configured for delivering the generated laser beam to the target area of tissue to provide a dermatological treatment.

47 Claims, 7 Drawing Sheets

(56) References Cited

U.S. PATENT DOCUMENTS

2009/0069741 A1 3/2009 Altshuler et al. ............... 604/22
2012/0253334 A1 10/2012 Liu et al. ........................ 606/9

OTHER PUBLICATIONS

International Search Report and Written Opinion, Application No. PCT/US2012/066261, 10 pages, Feb. 19, 2013.
Technical Specification for Giga GD20483 Laser Diode, 5 pages, 1999.
Technical Specification for JDS Uniphase RL30 Series, 4 pages, 2001.
Piprek et al., "What Limits the Output Power of Long-Wavelength AlGaInAs/InP Laser Diodes," IEEE Journal of Quantum Electronics, vol. 38, No. 9, 7 pages, Sep. 2002.
Ikoma, N. et al., "Highly Reliable AlGaInAs Buried Heterostructure Lasers for Uncooled 10Gb/s Direct Modulation," Optical Fiber Communications Conference Technical Digest, IEEE, XP010831967, 3 pages, Mar. 6, 2005.
International Search Report and Written Opinion, Application No. PCT/US2013/024287, 13 pages, Apr. 26, 2013.

\* cited by examiner

DERMATOLOGICAL TREATMENT DEVICE WITH ONE OR MORE LASER DIODE BAR

CROSS-REFERENCE TO RELATED APPLICATIONS

This application claims the benefit of U.S. Provisional Application No. 61/469,316 filed on Mar. 30, 2011; U.S. Provisional Application No. 61/533,641 filed on Sep. 12, 2011; U.S. Provisional Application No. 61/533,677 filed on Sep. 12, 2011; U.S. Provisional Application No. 61/533,786 filed on Sep. 12, 2011; U.S. Provisional Application No. 61/545,481 filed on Oct. 10, 2011; U.S. Provisional Application No. 61/563,491 filed on Nov. 23, 2011, all of which disclosures are herein incorporated by reference in their entirety.

TECHNICAL FIELD

The present disclosure is related to dermatological treatment devices that include one or more laser diode bars, e.g., high fill-factor laser diode bars.

BACKGROUND

Laser-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering laser radiation to an area of tissue on a person's body, e.g., the skin or internal tissue, to treat the tissue in a photochemical, photobiological, thermal, or, other manner, which can be ablative or non-ablative, among other properties, depending on the particular application.

Laser-based treatment devices may include any suitable type of laser, e.g., laser diode, fiber laser, VCSEL (Vertical Cavity Surface Emitting Laser), LED, etc. A device may include a single laser or multiple lasers, e.g., a laser diode bar including multiple distinct emitters arranged in a row, or multiple fiber lasers arranged in a row or array.

Diode lasers are particularly suitable for certain treatments and devices for providing such treatments. For example, diode lasers are compact, as they are typically built on one chip that contains all necessary components. Further, diode lasers typically provide an efficiency of up to 50%, which enables them to be driven by low electrical power compared to certain other lasers. Further, diode lasers allow direct excitation with small electric currents, such that conventional transistor based circuits can be used to power the laser.

Other characteristics of diode lasers include high temperature sensitivity/tunability, and a highly divergent beam compared to certain other lasers. Diode lasers typically emit a beam having an axis-asymmetric profile in a plane transverse to the optical axis of the laser. In particular, the emitted beam diverges significantly faster in a first axis (referred to as the "fast axis") than in an orthogonal second axis (referred to as the "slow axis"). In contrast, other types of lasers, e.g., fiber lasers, typically emit a beam having an axis-symmetric profile in the transverse plane.

Laser-baser treatment devices include larger-scale devices typically operated by a physician or other professional in a clinic or other office, as well as hand-held devices for home-use, allowing users to provide treatment to themselves. Some hand-held laser-baser treatment devices are battery powered, e.g., using a Li ion battery cell (or multiple cells). Such battery-powered devices may be recharged between use, e.g., by plugging into an A/C wall outlet, either directly or by docking in a docking unit plugged into the wall.

Some laser-baser treatment devices apply laser radiation directly from the laser source to the target tissue to create a pattern of radiated areas (e.g., spots, lines, or other shapes) in the tissue. Others include optics between the laser source and the target tissue. Such optics may include optical elements such as lenses, mirrors, and other reflective and/or transmissive elements, for controlling optical parameters of the beam, such as the direction, shape (e.g., convergent, divergent, collimated), spot size, angular distribution, temporal and spatial coherence, and/or intensity profile of the beam. Some devices include systems for scanning a laser beam in order to create a pattern of radiated areas (e.g., spots, lines, or other shapes) in the tissue. For some applications, the scanned pattern of radiated areas overlap each other, or substantially abut each other, or are continuous, in order to provide generally complete coverage of a target area of tissue. For other applications, e.g., certain wrinkle treatments and other skin rejuvenation treatments, the scanned radiated areas may be spaced apart from each other such that only a fraction of the overall target area of the tissue is radiated. In this case, there are generally regions of untreated tissue between regions of treated tissue. This latter type of treatment is known as "fractional" treatment (or more specifically, fractional photothermolysis) because only a fraction of the target area is irradiated.

Laser-baser treatment devices may deliver radiation as continuous wave (CW) radiation, manually pulsed radiation, automatically pulsed radiation, or in any other manner, and according to any suitable parameters, e.g., wavelength, current, power level, etc. For example, a wavelength of about 650 nm to about 1100 nm (e.g., about 810 in some applications) may be used for hair removal treatment. As another example, wavelengths absorbed by water in the skin, e.g., between 1400 nm and 2000 nm, may be used for certain treatments. For certain "fractional" skin treatments, a wavelength of about 1450-1550 nm±50 nm may be used, with a total energy of about 2 mJ-30 mJ delivered to the target tissue at each treatment zone, or "microthermal zone" (MTZ).

SUMMARY

In some aspects or embodiments of the present disclosure, a dermatological treatment device includes a device body; a laser diode bar configured to generate laser radiation for delivery to a target area of tissue, the laser diode bar having a fill factor of at least 50%; a power source; and control electronics configured to provide power from the power source to the laser diode bar such that the laser diode bar generates a laser beam; wherein the device is configured for delivering the generated laser beam to the target area of tissue to provide a dermatological treatment.

In some aspects or embodiments of the present disclosure, a dermatological treatment device includes a device body; a laser diode bar configured to generate laser radiation for delivery to a target area of tissue; and a power source and control electronics configured to provide power to the laser diode bar such that the laser diode bar generates a laser beam; wherein the device is configured for delivering the generated laser beam to the target area of tissue to provide a dermatological treatment; and wherein the device includes no optics downstream of the laser diode bar.

In some aspects or embodiments of the present disclosure, a dermatological treatment device includes a device body; a laser diode bar configured to generate laser radiation for delivery to a target area of tissue; a power source and control electronics configured to provide power to the laser diode bar such that the laser diode bar generates a laser beam for delivery to the target area of tissue; and an application end configured to be moved across the surface of the skin during delivery of the laser beam to the target area of tissue to provide a dermatological treatment.

BRIEF DESCRIPTION OF THE DRAWINGS

Some embodiments of the disclosure may be understood by referring, in part, to the following description and the accompanying drawings wherein.

DETAILED DESCRIPTION OF THE DRAWINGS

Figure 1:
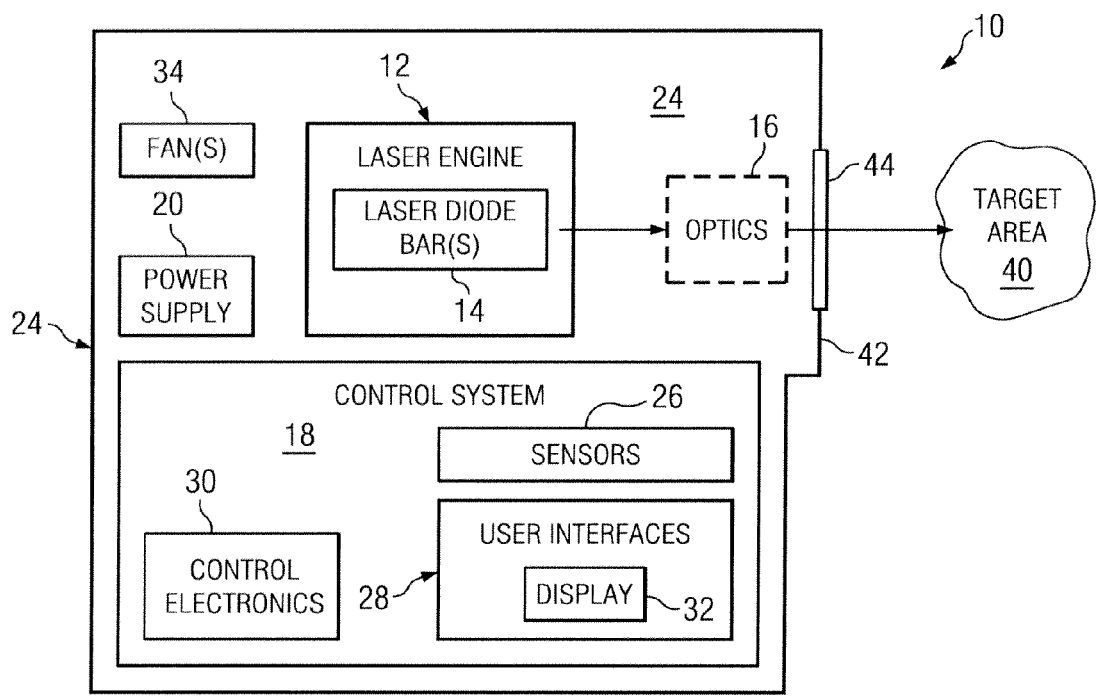
FIG. 1 illustrates components of an example treatment device including one or more laser diode bar line sources, according to certain embodiments

Some embodiments of the disclosure may be understood by referring, in part, to the following description and the accompanying drawings, in which like reference numbers refer to the same or like parts.

Treatment coverage rate is typically an important performance parameter for many skin treatment devices, such as laser hair removal devices, for example. "Gliding" treatment (wherein the treatment device is manually glided or slided along the skin surface, e.g., similar to a razor) with a radiation source configured to deliver radiation in a continuous or discontinuous line (referred to herein as a "radiation line source") may be an effective way to achieve a high coverage rate. Beam uniformity is also an important performance parameter in some light-based dermatological systems, e.g., for treatment efficacy and/or safety. Moreover, in some systems, increasing or maximizing optical throughput may be important for obtaining a target peak laser power and/or for reducing costs. Still further, eye safety is an important aspect of many light-based treatment devices, especially for consumer-use devices. Thus, features and embodiments disclosed herein may address one or more of the issues discussed above.

In some embodiments of the present disclosure, a dermatological treatment device and method incorporates at least one laser diode bar as a radiation line source, referred to herein as a "laser diode bar line source.". For some applications, using laser diode bar line source(s) may provide one or more advantages as compared to individual laser diodes, e.g., providing a high coverage rate, beam uniformity, and/or optical throughput. Devices including laser diode bar line source(s) may be configured for "direct exposure" or "in direct exposure," and/or configured as "close proximity" or "remote proximity" devices, depending on the particular embodiment. Certain embodiments configured as "direct exposure" and/or "close proximity" devices may provide at least some of the advantageous properties discussed above, among others.

In some embodiments, the laser diode bar line source (or each laser diode bar line source) may be a "high-fill factor" laser diode bar. As used herein, "high fill-factor" means a fill-factor of at least 50%, as compared to a "low-fill factor," defined as a till-factor of less than 50%. The fill factor is defined as the total emitter active portion of the laser diode bar divided by the width of the entire laser diode bar. For some applications, using high fill-factor laser diode bars may provide one or more advantages as compared to low fill-factor laser diode bars, e.g., providing an increased beam uniformity delivered to the target, which may be advantageous.

A particular example embodiment discussed below is a compact, direct exposure device that uses a high fill-factor laser diode bar to generate an eye-safe laser line source for hair removal treatments.

Basic Operation

A typical laser diode bar has a beam divergence of near 40° full angle in one direction parallel to the epitaxial growth axis (referred to as the fast axis). In particular, the beamlets emitted from each of the multiple discrete emitters of the laser diode bar has a beam divergence of near 40° in the fast axis direction. In contrast, the beamlets emitted from each of the multiple discrete emitters of the laser diode bar diverges much less rapidly in the slow axis (orthogonal to the fast axis), e.g. with a divergence of about 10° full angle.

Due to the rapid divergence in the fast axis direction, the laser diode bar provides a significant beam spread in this fast axis direction, in the absence of optical elements provided downstream of the laser diode bar. Therefore, in order to capture a desired portion of the beam energy (and/or maintain a desired beam intensity), certain embodiments are configured as "close proximity" devices, in which the "proximity gap spacing" is less than or equal to 10 mm. As used herein, the "proximity gap spacing" or "PGS" is defined as the distance between the emitting surface of the radiation source (in this case, the laser diode bar) and the skin-contacting surface of device 10, i.e., the distance between the emitting surface of the laser diode bar and the skin during a treatment position of device 10 on the skin.

In some embodiments, the proximity gap spacing is less than or equal to 10 mm, 5 mm, 2 mm, or even 1 mm. In particular embodiments, the proximity gap spacing is less than 500 µm, less than 200 µm, or even less than 10 µm. The proximity gap spacing may be selected based on one or more parameters, e.g., the desired size and/or intensity of treatment zones on the skin, and/or manufacturing constraints or costs.

Figure 5:
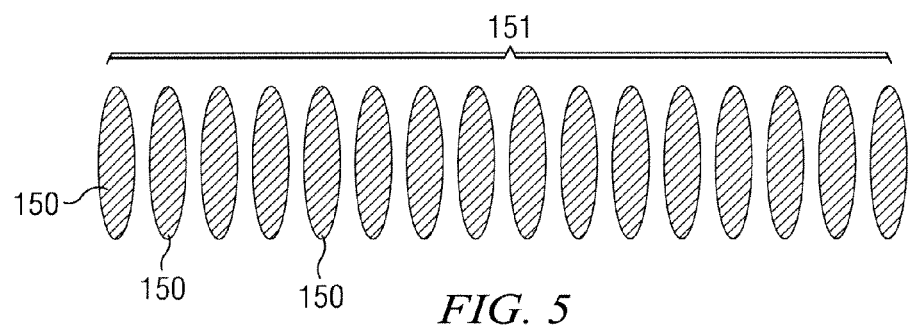
FIG. 5 illustrates a simulated beam profile at a target plane, as generated by an example laser diode bar with a 29% fill factor (low fill-factor).

However, in close proximity configurations, the delivered beam profile may be non-uniform in the slow-axis direction (perpendicular to the fast axis direction), due to the relatively slow divergence in the slow axis of the individual beamlets emitted from the multiple discrete emitters of the laser diode bar. For example, the delivered radiation may include multiple essentially discreet images, each corresponding to one of the multiple discrete emitters of the laser diode bar, e.g., as shown in FIG. 5. Such radiation profile at the target surface may be suitable or advantageous for some applications, but less suitable or disadvantageous for other applications, e.g., applications in which beam uniformity is advantageous.

In one example implementation of a battery-powered device having a target peak power close to 30 W, the device is configured as a close proximity device with a proximity gap spacing of less than 1.5 mm. At this spacing, a laser diode bar with a fill-factor of less than 50% would yield discrete laser emitter source images at the target plane. For example, a typical 808-nm laser bar with 29% fill factor may produce a non-uniform treatment zone pattern as shown in FIG. 5, discussed below. This non-uniform treatment zone pattern may be unsuitable or undesirable for effectively providing certain types of treatment at and/or below the skin surface, and/or may be unsuitable or undesirable for eye safety and/or skin safety reasons.

Figure 4:
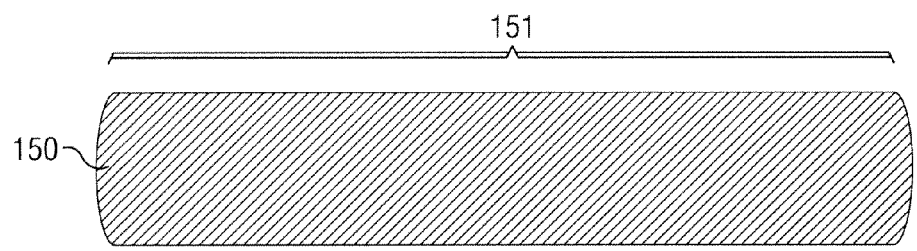
FIG. 4 illustrates a simulated beam profile at a target plane, as generated by an example laser diode bar with a 69% fill factor (high fill-factor).

In contrast, a high fill-factor laser bar (i.e., having a fill factor of at least 50%) may provide a more uniform treatment zone pattern at the target surface. For example, an expected treatment zone provided by a laser diode bar with a 69% fill-factor bar is shown in FIG. 4, discussed below. As shown, the treatment zone from the high fill-factor laser diode bar, even in a close proximity arrangement, is a substantially uniform elongated shape, referred to herein as a line segment. Such uniform line segment may be suitable or desirable for certain applications or treatments, e.g., a manual gliding treatment normal to the line segment direction (e.g., for laser hair removal, bulk heating skin tightening, or other suitable treatments. In some embodiments, the high fill-factor laser diode bar is used in conjunction with a translation sensor (e.g., a displacement sensor or a glide speed sensor) to allow a treatment dose to be metered uniformly over a relatively large area.

Some embodiments of the present disclosure include high fill-factor laser diode bar(s) in a "direct exposure" and/or "close proximity" configuration. Such embodiments may provide a uniform line segment treatment zone or image at the target surface. Some direct exposure and/or close proximity embodiments may require no precision aligned optics, and may provide a high optical throughput and be capable of generating high-power source in a compact battery-operated device. Some direct exposure and/or close proximity embodiments may be particularly compact. Further, in some embodiments, the laser diode bar may provide opaque and high-thermal conductivity metallic material close to the laser aperture for effective skin thermal management. Other embodiments, referred to as "indirect exposure" configurations, may include one or more fast axis optical elements for capturing and/or focusing the rapidly diverging fast axis beam profile emitted from the laser diode bar, as discussed below.

In some embodiments, laser diode bars as disclosed herein may be employed as laser diode bars in any of the various embodiments and configurations, incorporating any of the various features, functionality, and operational aspects, and for providing any of the various treatments as disclosed in U.S. patent application Ser. No. 13/366,246 filed Feb. 3, 2012 (hereinafter, "U.S. Ser. No. 13/366,246"), which disclosure is hereby incorporated by reference in its entirety.

FIG. 1 illustrates components of an example treatment device 10, according to certain embodiments. treatment device 10 may include a laser engine 12 including one or more laser diode bars 14 configured to generate one or more laser beams, optics 16 for delivering the laser beam(s) to a target area 40 (e.g., an area of tissue), a control system 18, one or more power supplies 20, and one or more fans 34.

As discussed below, "direct exposure" embodiments may omit optics 16 such that no optics are provided between laser diode bar 14 and the target surface, for direct exposure of the target tissue. In some direct exposure embodiments, laser diode bar 14 is located in close proximity to the target skin surface (e.g., less than 10 mm, less than 2 mm, or even less than 1 mm from the target skin surface).

The components of device 10 may be provided in a structure or housing 24, or alternatively may be provided in separate structures or housings and connected in any suitable manner, e.g., via fiber optic or other cabling. Housing 24 may define an application end (or "treatment tip") 42 configured to be placed in contact with the target surface (e.g., skin) during treatment of the target area 40. Application end 42 may include or house various user interfaces, including the treatment delivery interface for delivering output beams 94 to the user, as well as one or more sensors 26 for detecting various characteristics of the target surface and/or treatment delivered by device 10. In some embodiments, application end 42 may include an aperture or window 44 through which the laser beam is delivered to the target surface, or alternatively, an optical element 16 (e.g., a lens) may be located at application end 42 and configured for direct contact or very close proximity with the skin during treatment.

Device 10 may include any other components suitable for providing any of the functionality discussed herein or other related functionality known to one of ordinary skill in the art.

Laser engine 12 may include one or more laser diode bars 14. Where device 10 includes multiple laser diode bars 14, the multiple laser diode bars 14 may be arranged proximate each other and/or connected to each other, or may be spaced apart from each other.

The laser diode bar(s) 14 of device 10 may be configured for and/or operated at any suitable wavelength to provide the desired treatment. For example, laser diode bar(s) 14 may be configured for and/or operated at a wavelength of about 810 nm (e.g., 810 nm±30 nm) for providing hair removal treatment. As another example, laser diode bar(s) 14 may be configured for and/or operated at a wavelength that is absorbed by water in the skin, e.g., between 1400 nm and 2000 nm, e.g., for certain photothermolysis treatments. In some embodiments, laser diode bar(s) 14 may be configured for and/or operated at a wavelength of between 1400 nm and 1550 nm, e.g., for acne treatment or certain fractional non-ablative skin treatments. In other embodiments, laser diode bar(s) 14 may be configured for and/or operated at a wavelength of between 1700 nm and 1800 nm, e.g., for sebaceous gland related treatment like acne. In still other embodiments, laser diode bar(s) 14 may be configured for and/or operated at a wavelength of between 1900 nm and 1950 nm, e.g., for pigmented lesion treatment like solar lentigo.

Further, laser diode bar(s) 14 may be configured or operated to deliver continuous wave (CW) radiation, pulsed radiation, or in any other manner. In some embodiments, device 10 controls laser diode bar(s) 14 to provide CW radiation, e.g., for using device 10 in a gliding mode to provide bulk heating skin tightening, hair removal, or acne treatment. In other embodiments, device 10 controls laser diode bar(s) 14 to provide manually pulsed radiation, e.g., for using device 10 in a stamping mode to provide hair removal. In still other embodiments, device 10 controls laser diode bar(s) 14 to provide automatically pulsed radiation, e.g., for using device 10 in a gliding mode to provide selective photothermalysis. For example, in some embodiments, device 10 may be configured to sequentially deliver a series of laser beams (specifically, collective beams 94 discussed below) to the target area 40 to generate treatment zones (e.g., continuous or discontinuous line segments) that are spaced apart from each other by areas of non-irradiated skin between the adjacent treatment zones, to provide a fractional treatment to the tissue, e.g., for skin rejuvenation, wrinkle treatment, or treatment of pigmented legions (e.g., age spots, sun spots, moles, etc.).

Certain embodiments of device 10 include one or more optics 16 downstream of laser diode bar 14 for directing or treating the beam 94 emitted from laser diode bar 14 before reaching the target surface. Optics 16 may allow for laser diode bar 14 to be positioned at any desired distance from the application end 42 of the device that contacts the skin during treatment (and thus at any desired distance from the target surface). Embodiments of device 10 that include optics 16 downstream of laser engine 12 are referred to herein as "indirect exposure" embodiments.

Optics 16 may include any number and types of optical elements, e.g., lenses, mirrors, and other reflective and/or fully or partially transmissive elements, for delivering the light generated by laser engine 12 to the target area 40 and, if desired, for treating the beam, such as adjusting the treatment zone size, intensity, treatment zone location, angular distribution, coherence, etc. In some embodiments, optics 16 may include a scanning system for scanning a pattern of treatment zones in the target area 40, as discussed below. Beam treatment optics may be included before and/or after the scanning system or may be interspersed with the scanner or part of the scanning system.

As used herein, an "optic" or "optical element" may mean any element that deflects a light beam, influences the angular distribution profile (e.g., angle of convergence, divergence, or collimation) of a laser beam in at least one axis, influences the focus of the beam in at least one axis, or otherwise affects a property of the radiation. Thus, optics include mirrors and other reflective surfaces, lenses, prisms, light guides, gratings, filters, etc. For the purposes of this disclosure, optics do not generally include planar or substantially planar transmissive elements such as transmissive windows or films, such as those that serve as transmissive aperture that protect internal components.

Other embodiments of device 10 do not include any optics 16 downstream of laser diode bar 14. Such embodiments are referred to herein as "direct exposure" embodiments. A "direct exposure" embodiment or configuration does not include any optics downstream of the laser diode bar(s) 14 for affecting or treating the beam(s) generated by laser diode bar(s) 14. Some direct exposure devices may include a window (e.g., to protect the laser diode bar and/or other internal components of the device) that does not substantially affect the beam(s). A window may be formed from any suitable material, e.g., sapphire, quartz, diamond, or other material transparent at the frequency of the laser diode bar 14 and preferably also having a good thermal coefficient.

Because laser diodes typically emit a divergent beam, the laser diode bar 14 may be positioned very close to the application end 42 of the device that contacts the skin during treatment (and thus very close to the target surface). For example, some direct exposure devices are also configured for "close proximity" radiation, in which the laser diode bar 14 is positioned such that the emitting surface 80 is less than 10 mm from the leading surface of the application end 42 (and thus less than 10 mm from the target surface when the application end 42 is placed in contact with the skin). In some embodiments, the laser diode bar 14 is positioned such that the emitting surface 80 is less than 2 mm from the leading surface of the application end 42/less than 2 mm from the target surface. In particular embodiments, the laser diode bar 14 is positioned such that the emitting surface 80 is less than 1 mm from the leading surface of the application end 42/less than 1 mm from the target surface. Still further, in some embodiments, the laser diode bar 14 is positioned such that the emitting surface 80 is less than 500 μm, 200 μm, or even 100 μm from the leading surface of the application end 42 or the target surface. Control system 18 may be configured to control one or more components of device 10 (e.g., laser engine 12 and/or a beam scanning system 142). Control system 18 may include, for example, any one or more of the following: a laser control system for controlling aspects of the generation and delivery of laser beams to the user; in embodiments with a scanning system for scanning a beam to generate a pattern of treatment zones on the target skin area, a scanning system control system for controlling the scanning system; a displacement-based control system for controlling aspects of device 10 based on the determined displacement of device 10 across to the skin (e.g., as device is glided across the skin during treatment), e.g., relative to a prior treatment position; a temperature control system; an eye safety control system to help prevent exposure of the eyes (e.g., the corneas) to the treatment radiation (an eye safety control system may be omitted in embodiments in which the laser radiation emitted from device 10 is inherently eye-safe, e.g., certain direct exposure embodiments of device 10); and/or a battery/power control system.

Control system 18 may include one or more sensors 26, user interfaces 28 for facilitating user interaction with device 10, and control electronics 30 for processing data (e.g., from sensors 26 and/or user interfaces 28) and generating control signals for controlling various components of device 10. Control electronics 30 may include one or more processors and memory devices for storing logic instructions or algorithms or other data. Memory devices may include any one or more device for storing electronic data (including logic instructions or algorithms), such as any type of RAM, ROM, Flash memory, or any other suitable volatile and/or non-volatile memory devices. Logic instructions or algorithms may be implemented as software, firmware, or any combination thereof. Processors may include any one or more devices, e.g., one or more microprocessors and/or microcontrollers, for executing logic instructions or algorithms to perform at least the various functions of device 10 discussed herein. Control electronics 30 may include exclusively analog electronics or any combination of analog and digital electronics.

In some embodiments, control system 18 may include any of the various sensors and/or control systems disclosed in U.S. Ser. No. 13/366,246. For example, control system 18 may include one or more displacement sensor 100 (e.g., displacement sensor 100A, 100B, 100C, or 100D), motion/speed sensor 102, skin-contact sensor 104, pressure (or force) sensor 106, temperature sensor 108, radiation sensor 110, color/pigment sensor 112, eye safety sensor 114, dwell sensor 116, and/or roller-based sensor 118, as disclosed in U.S. Ser. No. 13/366,246. As another example, control system 18 may include any or all of a radiation source control system 130, a displacement-based control system 132, a user interface control system 134, a temperature control system 136, and/or a battery/power control system 138, as disclosed in U.S. Ser. No. 13/366,246.

Control system 18 may control components or aspects of device 10 based on feedback from sensors 26, user input received via user interfaces 28, and/or logic instructions/algorithms. For example, in some embodiments, control system 18 may control the operation of laser engine 12 and/or component(s) of a beam scanning system (e.g., a rotating scanning element) based at least on feedback from a displacement sensor for detecting the displacement of device 10 relative to the skin 40 as the device is moved across the skin. Thus, for example, control system 18 may control laser engine 12 and/or a rotating scanning element based on signals from a displacement sensor indicating that device 10 has moved a certain distance across target area 40 from a prior treatment position. As another example, control system 18 may control the operation of laser engine 12 and/or component(s) of a beam scanning system (e.g., a rotating scanning element) based at least on feedback from a glide speed sensor for detecting the speed of device 10 moving across the skin. Thus, for example, control system 18 may control laser engine 12 and/or a rotating scanning element based on signals from a glide speed sensor indicating that device 10 is moving at a particular speed across the skin 40.

More specifically, control system 18 may be configured to control one or more operational parameters of device 10. For example, control system 18 may control the treatment level (e.g., low power level, medium power level, or high power level) or treatment mode (e.g., gliding mode vs. stamping mode; or manually pulsed mode vs. automatically pulsed mode; or rapid-pulse mode vs. slow-pulse mode; or initial treatment mode vs. subsequent treatment mode; etc.), the status of laser diode bar 14 (e.g., on/off, pulse-on time, pulse-off time, pulse duty cycle, pulse frequency, temporal pulse pattern, etc.), parameters of the radiation (e.g., radiation wavelength, intensity, power, fluence, etc.), the configuration or operation of one or more optical elements (e.g., the operation of a rotating-element beam scanning system 142, as discussed below), and/or any other aspects of device 10.

Sensors 26 may include any one or more sensors or sensor systems for sensing or detecting data regarding device 10, the user, the operating environment, or any other relevant parameters. For example, as discussed in greater detail below with respect to FIG. 2, sensors 26 may include one or more of the following types of sensors: (a) one or more displacement sensor for determining the displacement of device 10 relative to the skin as device 10 is moved (e.g., glided) across the skin, (b) one or more glide speed sensor for determining the speed, rate, or velocity of device 10 moving (e.g., gliding) across the skin, (c) one or more skin-contact sensor for detecting proper contact between device 10 and the skin, (d) one or more pressure sensor for detecting the pressure of device 10 pressed against the skin, (e) one or more temperature sensor for detecting the temperature of the skin, a region of the skin, and/or components of device 10, (f) one or more radiation sensor for detecting one or more parameters of radiation (e.g., intensity, fluence, wavelength, etc.) delivered to the skin, (g) one or more color/pigment sensor for detecting the color or level of pigmentation in the skin, (h) one or more treatment endpoint sensor, e.g., a color/pigment sensor, for detecting an influence of the radiation on the skin (e.g., erythema, temperature, perifollicular edema, etc.) during or after a treatment, (i) one or more eye safety sensor for preventing unwanted eye exposure to light from laser diode bar 14, (j) one or more dwell sensor for detecting if the device is stationary or essentially stationary with respect to the skin, (k) one or more roller-type sensors for detecting the displacement and/or glide speed of device 10, and/or any (l) other suitable types of sensors.

User interfaces 28 may include any systems for facilitating user interaction with device 10. For example, user interfaces 28 may include buttons, switches, knobs, sliders, touch screens, keypads, devices for providing vibrations or other tactile feedback, speakers for providing audible instructions, beeps, or other audible tones; or any other methods for receiving commands, settings, or other input from a user and providing information or output to the user. User interfaces 28 may also include one or more displays 32, one or more of which may be touchscreens for receiving user input. One or more user interfaces 28 or portions thereof may be included in a separate housing from the treatment device, such as in a smart charging dock or a personal computer, and the treatment device may communicate with the separate housing via hardwire (such as a cable or jack), wireless methods (such as infrared signals, radio signals, or Bluetooth), or other suitable communication methods.

Power supplies 20 may include any one or more types and instances of power supplies or power sources for generating or supplying power to the various components of device 10. For example, power supplies 20 may comprise one or more rechargeable or non-rechargeable batteries, capacitors, super-capacitors, DC/DC adapters, AC/DC adapters, and/or connections for receiving power from an outlet (e.g., 110V wall outlet). In some embodiments, power supplies 20 include one or more rechargeable or non-rechargeable batteries, e.g., one or more Li containing cells or one or more A, AA, AAA, C, D, prismatic, or 9V rechargeable or non-rechargeable cells.

Figure 2:
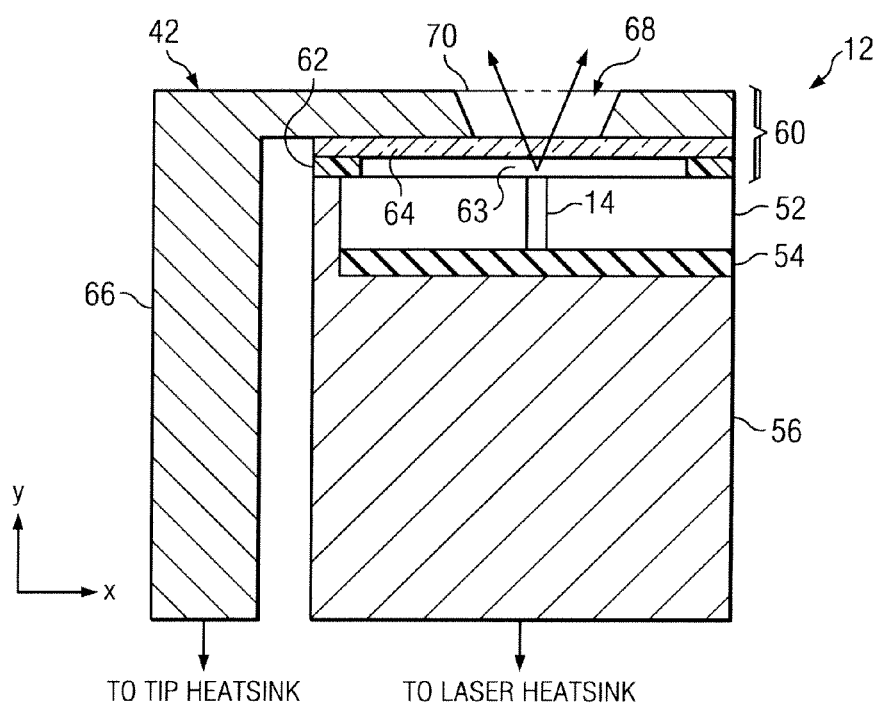
FIG. 2 illustrates a cross-sectional side view of an example laser diode bar, according to example embodiments of the present disclosure.

FIG. 2 illustrates a cross-sectional side view of a treatment tip 42 of device 10 that includes an example laser engine 12 with a laser diode bar 14, according to example embodiments of the present disclosure. Laser engine 12 includes laser diode bar 14 assembled next to a set of CuW alloy contact submounts 52 on a metalized ceramic carrier 54. This laser engine 12 is attached to a heat sink post 56 for thermal management. Above the output surface of laser bar 14 is a stack 60 including a plastic spacer 62 (which may define a vacuum or open-air region 63 directly above the output surface of laser bar 14), a scattering diffuser 64, and a metal tip 66 defining an open aperture 68 through which the laser beam 94 is emitted. In other embodiments, stack 60 could include an output window 70 (indicated by dashed line) rather than an open aperture 68, among other variations. Window 70 may project beyond an outer surface of application end 42, may be arranged flush with the outer surface of application end 42, or may be recessed from the outer surface of application end 42. Window 70 may have any suitable thickness. For example, in some embodiments, window 70 has a thickness of between about 200 µm and 3 mm. In other embodiments, window 70 has a thickness of between about 100 µm and about 200 µm. In certain embodiments, window 70 is a thin film having a thickness of less than 150 µm, e.g., about 75 µm.

Further, it should be understood that the disclosed materials are examples only, and that any other suitable materials may be used.

The metal treatment tip 42 may be coupled to a separate heat sink system for possible thermal management of the skin, such as pre-cooling prior to laser exposure or heat transfer during or after laser exposure.

Stack 60 defines the proximity gap spacing between the laser diode bar 14 and the target plane. As discussed above, in some embodiments, the proximity gap spacing is less than or equal to 10 mm, 5 mm, 2 mm, or even 1 mm. In particular embodiments, the proximity gap spacing is less than 500 µm, less than 200 µm, or even less than 100 µm. For example, in some embodiments that include a diffuser 64 and a window 70, diffuser 64 has a thickness of between about 200 µm and about 1 mm, and window 70 has a thickness of between about 200 µm and about 2 mm. In a particular example embodiment, diffuser 64 has a thickness of about 0.4 mm, and window 70 has a thickness of between about 1 mm, such that stack 60 defines a proximity gap spacing of less than 2 mm (e.g., about 1.4 mm).

Scattering diffuser 64 in the tip stack 60 may be configured to achieve approximately Lambertian angular profile for eye-safe radiation (e.g., Class 1M or better per IEC 60825-1). Other embodiments may omit diffuser 64, thus resulting in a less scattered/more focused output beam, which may be suitable or advantageous for certain treatments, e.g., fractional treatments or ablative treatments.

In some embodiments or settings, device 10 meets the Class 1M or better such as Class 1) eye safety classification per the IEC 60825-1. In other embodiments or settings, the device falls outside the IEC 60825-1 Class 1M eye safety classification, but still provides a level of eye safety. Eye safety aspects are discussed below in the "Eye Safety" section.

Figure 3:
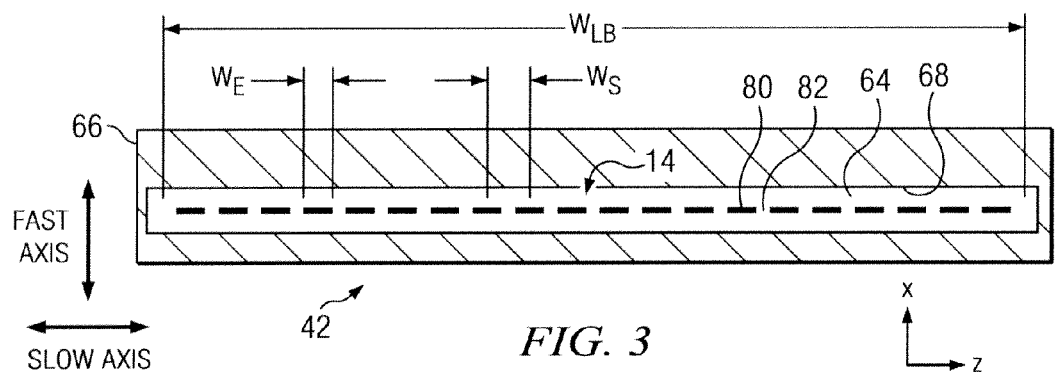
FIG. 3 illustrates a front view of the tip of the laser diode bar, indicating the aspects of the fill factor, according to example embodiments of the present disclosure.

FIG. 3 illustrates a front view of the example device treatment tip 42 shown in FIG. 2, according to example embodiments of the present disclosure. As shown, treatment tip 42 includes a metal tip 66 that defines an aperture 68 through which the beam 94 is emitted. Laser diode bar 14 is located below diffuser 64. Laser diode bar 14 includes any suitable number of active emitter regions (referred to simply as "emitters") 80 separated by non-active regions 82. Each emitter has a width $W_E$, and adjacent emitters 80 are area spaced apart (from center-to-center of adjacent emitters) by a distance $W_S$.

When laser diode bar 14 receives suitable power from power supply 20, each emitter 80 emits an individual beamlet. The beamlets of the multiple emitters 80 of the laser diode bar 14 are together referred to as collective beam 94. Each beamlet diverges significantly faster in the fast axis than in the slow axis, the direction of these axes being indicated in FIG. 3.

Laser diode bar 14 has a fill-factor defined by the total width of all emitters ($\Sigma W_E$) divided by the total width of the laser diode bar ($W_{LB}$).

In some embodiments, the fill-factor is equal to or above 50% (referred to herein as a "high fill-factor"). In some embodiments, the fill-factor is above 65%. In some embodiments, the fill-factor is above 75% (e.g., a fill-factor of about 80%). In particular embodiments, the fill-factor is above 85% (e.g., a fill-factor of about 90%). High fill-factor laser diode bars may generate a treatment image defining a contiguous, substantially uniform, elongated treatment zone (i.e., a contiguous line segment), extending in the direction of the laser diode bar, which may be advantageous for particular treatments, as discussed above. For example, FIG. 4 illustrates a simulated treatment image 151 is a single treatment zone 150 consisting of a contiguous line segment at a target plane generated by an example laser diode bar 14 having about 70% fill-factor with 69 emitters, emitter width $W_E$ of 100-µm, and center-to-center emitter spacing $W_S$ of 140-µm. As shown, the treatment zone defines an essentially uniform line segment In other embodiments, the fill-factor is below 50% (referred to herein as a "low fill-factor"). Such laser diode bars may generate a treatment zone that defines multiple discreet images, each corresponding to a different emitter 80 of the laser diode bar 14, which may be advantageous for particular treatments. In some embodiments, device 10 includes low fill-factor laser diode bar(s) configured or arranged such that the beamlets emitted from individual emitters 80 generate treatment zones on the target surface that are spaced apart from each other, e.g., to define a treatment image in the form of a non-contiguous line segment. In some embodiments, the multiple treatment zones generated by the multiple individual emitters 80 of the same laser diode bar are sufficiently spaced apart from each other to provide an effective fractional treatment (e.g., for skin resurfacing, wrinkle treatment, etc.).

For example, FIG. 5 illustrates a simulated image 151 of treatment zones 150 at a target plane generated by an example laser diode bar 14 having about 29% fill-factor with 19 emitters, emitter width $W_E$ of 150-µm, and center-to-center emitter spacing $W_S$ of 500-µm. As shown, the image 151 generally defines a non-contiguous line segment consisting of spaced-apart treatment zones 150. Each treatment zone 150 is generated by a separate emitter 80 of the laser diode bar 14. As shown, the treatment zones 150 are spaced apart from each other by essentially non-irradiated areas. The spacing of adjacent treatment zones may be selected based on the design of laser diode bar 14 (e.g., the fill-factor, the width $W_E$ of individual emitters 80 and the center-to-center spacing $W_S$ between adjacent emitters 80), the distance between the emitting surface and the target surface (e.g., the proximity gap spacing), optics between laser diode bar 14 and the target surface (if any), the power emitted by emitters 80, the wavelength emitted by emitters 80 (e.g., due to the wavelength-specific depth of treatment in the skin), and/or any other relevant parameter.

Figure 6:
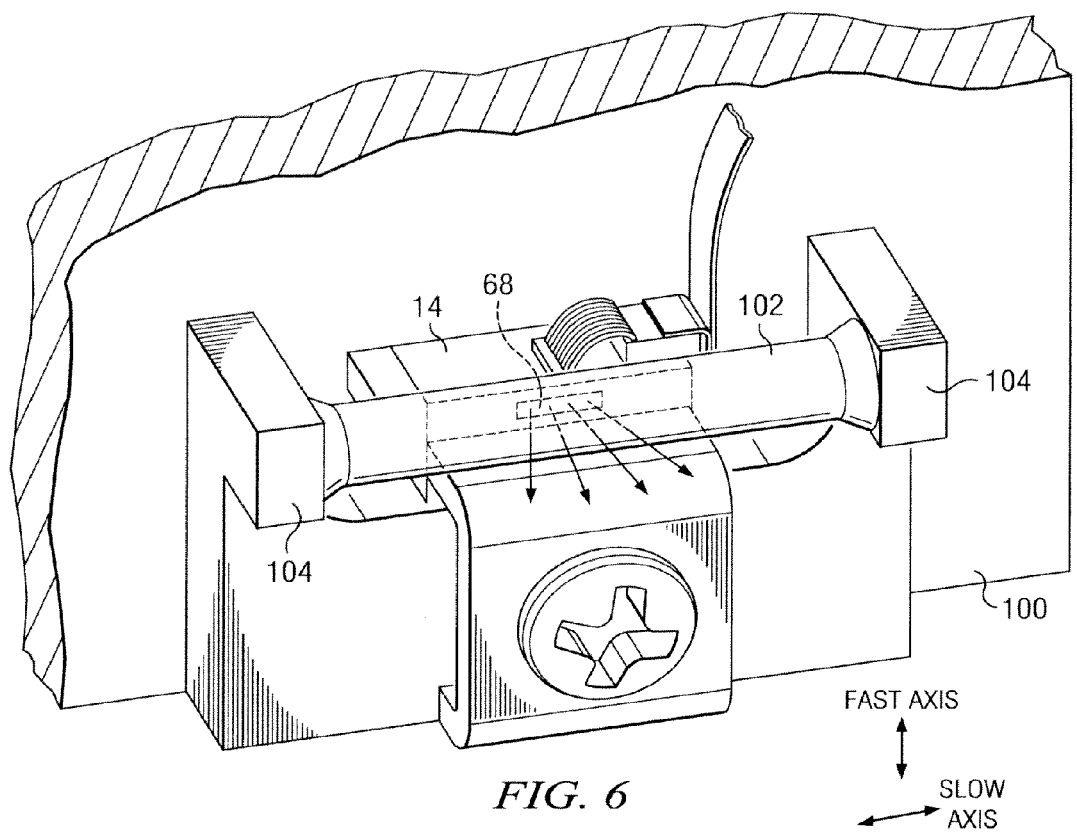
FIG. 6 illustrates a three-dimensional view of a portion of an example laser engine, according to certain embodiments of the present disclosure.

In some embodiments, low fill-factor laser diode bar 14 may generate treatment zones 150 (from individual emitters 80) that are separated from each by non-irradiated areas at least 0.5 mm wide. For instance, in some example embodiments, laser diode bar 14 has the following characteristics:

fill factor of about 15% to about 30%,
    center-to-center emitter spacing $W_S$ of about 1000 µm to about 500 µm,
    proximity gap spacing of less than 3 mm,
generates treatment zones 150 (from individual emitters 80) each having an effective spot area of about 0.25 mm², and are separated from each other by non-irradiated areas having a width of 0.5 mm to about 0.2 mm. FIG. 6 illustrates a three-dimensional view of a portion of an example laser engine 12 having a laser diode bar 14 (high fill-factor, or low fill-factor, depending on the embodiment), arranged in an "indirect exposure" configuration, according to an example embodiment. Laser engine 12 may include laser diode bar 14, a heat sink 100, a fast axis optic 102, and a securing system 104 for securing fast axis optic 102. Laser engine 12, in particular heat sink 100, may be mounted or connected to a printed circuit board (PCB). Laser diode bar 14 may be coupled to electronics on PCB by a suitable electrical connection, e.g., a flexible cable.

Heat sink 100 serves to cool laser diode bar 14 and may be fabricated via an extrusion process or in any other suitable manner. Some embodiments include one or more fans to help maintain the laser temperature at a desired level. Heat sink may include fins or other structures for promoting heat transfer. In some embodiments the heat sink may be passive and/or absorb and/or transfer heat by conduction only and/or combined with natural convection and/or combined with radiative heat transfer. In some embodiments, heat sink 100 in the fully assembled device 10 has a rating of about 2.5° C./W or lower. In particular embodiments, heat sink 100 in the fully assembled device 10 has a rating of about 1.5° C./W or lower.

In some embodiments, device 10 may also include one or more fans 34 to actively cool heat sink 100, to further promote heat transfer from laser diode bar 14 and/or other powered components of device 10.

Fast axis optic 102 may comprise any optic for affecting the fast-axis profile of collective beam 94 emitted from laser diode bar 14. For example, in the illustrated embodiment, fast axis optic 102 is a high numerical aperture (high NA) short focal length cylindrical lens (or "rod lens") arranged to reduce the angular divergence of collective beam 94 in the fast axis. In one embodiment, cylindrical lens 102 is about 2 cm long with a diameter of about 2 mm. However, lens 102 may have any other suitable dimensions. Further, in other embodiments, lens 102 may comprise a different shaped lens. For example, lens 102 may be an aspheric lens or a spherical lens.

Lens 102 may be secured to heat sink 100 in any suitable manner. For example, lens 102 may be mounted between a pair of support structures, which form a securing system 104 for securing the cylindrical lens 102 to heat sink 100. The support structures of securing system 104 may be integral with the body of heat sink 100, or otherwise coupled to heat sink 100. Lens 102 may be secured to the support structures in any suitable manner. For example, lens 102 may be positioned between the support structures and adhered to the support structures using UV adhesive, e.g., UV epoxy that is cured via a UV curing process. Cylindrical lens 102 may be positioned at any suitable distance from the emitter junctures/apertures of laser diode bar 14. In one embodiment, lens 102 is positioned about 260 um from the emitter junctures/apertures of laser diode bar 14.

Operation of Device 10

As discussed above, device 10 may be configured to deliver a laser beam 94 (or multiple beams 94) to a target area 40 to provide a desired treatment. Device 10 may deliver beam 94 to generate various treatment patterns in the target area 40. For example, various treatment patterns may be generated by any combination of the following: operating device 10 in a manual gliding mode, operating device 10 in a stamping mode, providing continuous wave (CW) radiation, providing pulsed radiation, providing direct exposure radiation, or providing indirect exposure radiation, e.g., including a scanning device to automatically scan the beam emitted from laser diode bar 14.

In some embodiments, device 10 controls laser diode bar 14 to provide CW or quasi-CW radiation, e.g., for bulk heating skin tightening, hair removal, or acne treatment by operating device 10 in a gliding mode.

In other embodiments, device 10 provides pulsed radiation. Pulsed radiation may include manually pulsed radiation or automatically pulsed radiation. In manually pulsed radiation, each pulse may be manually triggered, e.g., by pressing a button to initiate each pulse. In some embodiments, manually pulsed radiation used in a stamping mode. Manually pulsed radiation may be used for any suitable treatment, e.g., certain hair removal treatments.

Alternatively, in automatically pulsed radiation, pulses may be initiated or controlled automatically, e.g., according to a predefined pulse frequency or automatically upon some triggering event, such as automatic pulse triggering upon a predetermined displacement of device 10 moving across the skin, or automatic pulse triggering upon re-triggering of a capacitive skin contact sensor by lifting and placing the device tip on a different spot, for example. Automatically pulsed radiation may be provided in any suitable manner, e.g., by controlling laser diode bar 14, by intermittently blocking the energy beam emitted by laser diode bar 14, or otherwise. Such embodiments may utilize any suitable pulse parameters, e.g., pulse rate or frequency, pulse on time, pulse off time, duty cycle, pulse profile, etc. In some embodiments, laser diode bar 14 may be pulsed at a rate between 0.5 and 75 Hz. For example, laser diode bar 14 may be pulsed at a rate between 2 and 30 Hz. In particular embodiments, laser diode bar 14 may be pulsed at a rate between 10 and 20 Hz, e.g., about 15 Hz. The energy per pulse on a given treatment zone can be achieved by a single pulse or by multiple repetitive pulses. Automatically pulsed radiation may be used for any suitable treatment, e.g., fractional treatment.

As used herein, a "pulse" may include both (a) a single, continuous burst of radiation from laser diode bar 14, and (b) one or more higher-frequency pulses at substantially the same location on the skin (i.e., with substantially overlapping areas of irradiation at the skin surface), sometimes referred to as a modulated pulse, pulse train, or super pulse. If the time interval between the pulses in a pulse train is shorter than the relaxation time of the mechanism of action (e.g., shorter than the thermal relaxation time of a photothermolysis chromophore target), then the pulse train can deliver substantially similar results as a single longer pulse.

As used herein, a "treatment zone" (e.g., treatment zone 150) means a contiguous area of skin irradiated by one or more emitters 80—during a continuous period of irradiation or during a pulse (as defined above)—to a degree generally sufficient to provide a desired treatment in the skin at that location. The boundaries of a treatment zone may be defined by the "$1/e^2$ width," i.e., the treatment zone includes a contiguous area of the skin surface that is irradiated by a radiation intensity equal to at least $1/e^2$ (or 0.135) times the maximum radiation intensity at any point on the skin surface. Further, reference to a treatment zone "on the skin" or similar language refers to radiation pattern on the skin which generally produces a radiation pattern within the skin, whether or not it produces a treatment effect on the surface of the skin.

In some embodiments, e.g., as shown in FIGS. 4 and 5, treatment zones may define elongated line segments, either contiguous (FIG. 4) or non-contiguous (FIG. 5), depending on various factors, e.g., fill-factor, proximity gap spacing, optics between laser diode bar 14 and the treatment surface (if any), etc. Treatment zones may have any suitable dimension in the fast axis and slow axis direction, based on similar factors, as well as the design and dimensions of the laser diode bar 14 itself.

Figure 7:
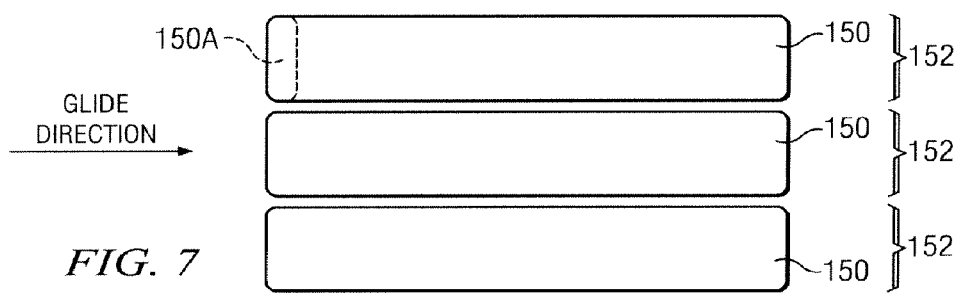
FIG. 7 illustrates an example treatment pattern generated by the example device having a high fill-factor laser diode bar, configured to provide continuous wave (CW) radiation and operated in a manual gliding mode, according to example embodiments of the present disclosure.

A treatment zone includes any increased areas due to smearing, blurring, or other elongation in any one or more direction due to movement of the device across the skin, whether the laser diode bar is providing pulsed or continuous wave (CW) radiation. For example, in embodiments or situations in which the irradiated area on the skin moves across the skin during delivery of the radiation (e.g., during a gliding mode operation of the device), the treatment zone includes the collective area swept by the moving irradiated area throughout a continuous (i.e., uninterrupted) period of radiation delivery to the skin. Thus, if device 10 is moved across the skin during CW radiation (e.g., in a gliding mode operation), a treatment zone may be many times larger than the size of the instantaneous irradiated area of skin, e.g., as shown in FIG. 7 and discussed below. If device 10 is moved across the skin during pulsed radiation (e.g., in a gliding mode operation), a treatment zone may be, for example, 10% to 500% larger than the size of the instantaneous irradiated area of skin, depending on a number of factors. In contrast, the example treatment zones 150 shown in FIGS. 4 and 5 assume a situation in which device 10 is held stationary on the skin (i.e., no smearing or blurring is indicated).

Each treatment zone on the surface of the skin may produce a three-dimensional volume of thermally damaged skin extending below the surface of the skin, which may be referred to as a micro thermal zone (MTZ). Each MTZ may extend from the skin surface downward into the skin, or may begin at some depth below the skin surface and extend further downward into the skin, depending on the embodiment, device settings, or particular application. The lateral dimensions of each MTZ may be co-extensive with the dimensions of the corresponding irradiated treatment zone, may be smaller than the corresponding irradiated treatment zone, or may be larger than the corresponding irradiated treatment zone (e.g., due to thermal conductivity).

MTZs may be provided for providing any suitable dermatological treatment, e.g., any of the treatments discussed herein. For example, in some applications, such as hair removal treatment, MTZs may be generated to cause thermal injury of hair follicles. In other applications, such as fractional treatment for example, MTZs may be generated to cause thermal injury to the skin, e.g., ablative or non-ablative lesions.

In some embodiments, device 10 is configured to be used in a "gliding mode" in which the device is manually dragged or glided across the skin while delivering continuous wave (CW), pulsed, and/or scanned radiation to the target area 40, to create continuous treatment zones in the direction of gliding, or alternatively to create rows or arrays of discreet treatment zones (spaced apart, touching, or overlapping) in the direction of gliding.

In other embodiments, device 10 is configured to be used in a "stamping mode" in which device 10 is held relatively stationary at different locations on the skin. At each location on the skin, device 10 may deliver one or more beams (or one or more automatically scanned rows or arrays of beam) to the skin to generate one or more treatment zones. Thus, device 10 may be positioned at a first location, one or more treatment zones may then be delivered to the skin while device 10 is held relatively stationary, device 10 may then be moved—by lifting device 10 and repositioning it or by gliding device 10 across the surface of the skin—to a new location, and one or more treatment zones may then be generated at that location, and so on, in order to cover a target area 40 as desired.

Direct Exposure Embodiments

As discussed above, some embodiments of device 10 are "direct exposure devices" that do not include any optics 16 downstream of laser diode bar 14 for affecting or treating the beam. Due to rapid divergence of beam 94 emitted from laser diode bar 14, the laser diode bar 14 may be positioned very close to the application end (or "tip") 42 of the device that contacts the skin during treatment (and thus very close to the target surface). For example, in direct exposure devices, the laser diode bar 14 may be positioned such that the emitting surface 80 is less than 10 mm, less than 2 mm, less than 1 mm, less than 500 μm, less than 200 μm, or even less than 100 μm from the leading surface of the application end 42 (and thus less than 10 mm, 2 mm, 1 mm, 500 μm, 200 μm, or even 100 μm from the target surface when the application end 42 is placed in contact with the skin), as discussed above.

As discussed above, some direct exposure embodiments of device 10 may be configured to provide CW radiation in a gliding mode. For example, a direct exposure embodiment of device 10 including a high fill-factor laser diode bar 14 may be operated in a CW mode while the device is manually dragged or glided across the skin in a direction generally perpendicular to the elongated direction of the laser diode bar, to generate a continuous treatment zone in the direction of gliding, having a width generally corresponding to the width of the laser diode bar, $W_{LB}$. The device may be glided multiple times across the skin at adjacent locations to cover a desired target area 40, e.g., to provide a hair removal treatment.

FIG. 7 illustrates an example treatment pattern generated by a direct exposure embodiment of device 10 including a high fill-factor laser diode bar 14, configured to provide CW radiation in a gliding mode, with the glide direction generally perpendicular to the elongated direction of the laser diode bar. The illustrated pattern includes three treatment zones 150, each formed by a separate manual glide 152 in the indicated glide direction. The initial treatment image at the beginning of the first glide (i.e., at the instant when the laser diode bar 14 is powered on) is indicated at 150A.

The treatment zones 150 are shown as separated from each other by a small distance. However, the user may control the position of each glide of device 10 such that the treatment zones 150 separated from each other by any desired amount, overlap each other by any desired amount, or are generally aligned edge-to-edge such that both overlapping and untreated gaps are substantially avoided. In some applications, the user may cover a target area 40 by gliding device 10 a suitable number of times generally in the same direction (e.g., as shown in FIG. 7). In other applications, the user may glide device 10 generally in a multiple directions, e.g., to form a criss-cross pattern or any other desired pattern of treatment of a target area 40, e.g., as recommended for the relevant treatment.

In other embodiments, a direct exposure embodiment of device 10 including a low fill-factor laser diode bar 14 may be operated in the same manner to generate a similar treatment pattern, but wherein each treatment zone 150 includes a series of continuous, thin treatment lines in the direction of gliding (each line corresponding to one emitter 80 of the laser diode bar 14).

Other direct exposure embodiments of device 10 may be configured to provide pulsed radiation in a gliding mode. For example, a direct exposure embodiment of device 10 including a high fill-factor laser diode bar 14 may be pulsed while the device is manually dragged or glided across the skin in a direction perpendicular to the elongated direction of the laser diode bar, to generate a series of spaced-apart continuous-segment treatment zones in the direction of gliding, e.g., to provide a fractional treatment for treating wrinkles, pigmentation and coarse skin caused by photodamage). The device may be glided multiple times across the skin at adjacent locations to treat a desired target area 40, e.g., to provide a fractional treatment. Alternatively, a direct exposure embodiment of device 10 including a low fill-factor laser diode bar 14 may be operated in the same manner to generate a series of spaced-apart discontinuous-segment treatment zones in the direction of gliding.

Figure 8:
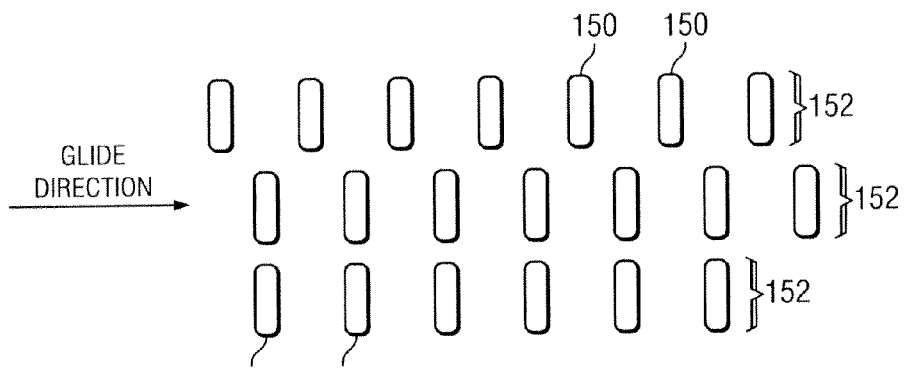
FIG. 8 illustrates an example treatment pattern generated by the example device having a high fill-factor laser diode bar, configured to provide pulsed radiation and operated in a manual gliding mode, according to example embodiments of the present disclosure.

FIG. 8 illustrates an example treatment pattern generated by a direct exposure embodiment of device 10 including a high fill-factor laser diode bar 14, configured to provide pulsed radiation in a gliding mode, with the glide direction generally perpendicular to the elongated direction of the laser diode bar. The illustrated pattern includes three rows of multiple treatment zones 150, each row formed by a separate manual glide 152 in the indicated glide direction, thus providing an array of spaced-apart treatment zones 150, each treatment zone 150 produced by a single pulse of laser diode bar 14. As discussed above, the relative spacing and direction of each manual glide 152 may be controlled as desired by a user, e.g., as recommended for the relevant treatment (e.g., a fractional treatment).

In some embodiments, the laser diode bar 14 is pulsed with a pulse rate set or selected based on a typical or expected speed at which the device is manually glided across the skin ("glide speed"). In particular, the pulse rate may be set or selected such that for a range of typical or expected manual glide speeds, adjacent treatment zones are physically separated from each other by areas of non-treated skin (i.e., fractional treatment is provided). In some embodiments, the pulse rate may be set or selected such that for a range of typical or expected manual movement speeds, adjacent treatment zones are physically separated from each other from a predetermined minimum non-zero distance, e.g., 500 μm.

In some embodiments, laser diode bar 14 may be pulsed at a rate between 0.5 and 75 Hz. For example, laser diode bar 14 may be pulsed at a rate between 2 and 30 Hz. In particular embodiments, laser diode bar 14 may be pulsed at a rate between 10 and 20 Hz, e.g., about 15 Hz. The energy per pulse on a given treatment zone can be achieved by a single pulse or by multiple repetitive pulses. In some embodiments, the device may be controlled to prevent or reduce the incidence or likelihood of treatment zone overlap, e.g., based on feedback from one or more sensors (e.g., a dwell sensor, motion sensor, displacement sensor, and/or roller-type sensor). In some embodiments, the pulse rate may be automatically adjustable by the device and/or manually adjustable by the user, e.g., to accommodate different manual movement speeds and/or different comfort levels or pain tolerance levels of the user. Some embodiments include other devices or techniques that individually or in combination provide over-treatment protection, e.g., to prevent pulse stacking, firing on the same area, an excessive treatment zone 150 density, or other non-desirable treatment conditions. For example, the device may cease to operate (e.g., generate beams) when stationary. A stationary condition may be measured by signal change induced by motion or lack of motion in capacitive, optical reflection, remittance, or scattering variation, acoustical reflection variation, acoustical impedance, galvanic potential, potential difference, dielectric constant variation, thermal variation, and so on.

As another example, a stationary condition may further be measured by local pyrometry. The treatment beam area is optically measured by "local thermal imaging". Local heating above a threshold indicates loss of motion. A stationary condition may further be measured by bulk heating measurement. If the tip of the treatment delivery device begins to heat above a threshold, loss of motion is detected, or excessive treatment in the area is detected.

As another example, the device may fire an "encouragement pulse" when stationary. A single non-damaging but higher than normal energy pulse or brief pulse train is emitted if the device becomes stationary to encourage the user to move on.

As another example, the device may deliver heat or cold to encourage motion. Dwelling in one place would become uncomfortable. As another example, mechanical rollers may detect a non-motion condition. Motorized rollers may drive motion physically avoiding a non-motion condition.

As yet another example, the output pulse frequency or energy may be adjusted to compensate for displacement speed reduction or cessation so as to avoid insufficient spacing of treatment zones, pulse stacking, or generalized over-treatment.

Any of the over-treatment protection systems or techniques described above (expect those directly concerned with pulse parameters) may be similarly incorporated in any CW radiation embodiment, e.g., for a hair removal device.

Some direct exposure embodiments of device 10 include a single laser diode bar 14. Other embodiments include multiple laser diode bars 14. As discussed above, the beam 94 emitted from each laser diode bar 14 diverges in both a fast axis and a slow axis. Thus, in such embodiments, if the device includes no optics downstream of the laser diode bar(s) 14, each beam 94 exits the application end of the device, and reaches the target surface as a diverging beam. As discussed below, this may provide an aspect of eye-safety, e.g., as discussed below. In some embodiments, the arrangement of laser diode bar(s) 14 and/or the divergence of the beam(s) 94 emitted from laser diode bar(s) 14 may provide sufficient eye safe radiation such that an eye safety sensor or system may be omitted, e.g., as discussed below.

As discussed above, laser diode bar 14 may be selected or configured to emit a beam of any suitable wavelength, power, and energy level. Further, the total energy emitted by laser diode bar 14 may be selected or configured as desired.

In some example direct exposure embodiments, assuming a total optical efficiency from laser diode bar 14 to the target surface of between about 70% and about 90%, laser diode bar 14 is configured to deliver a total energy of between about 40 mJ and about 2 J per treatment zone, assuming for example a pulsed operation with a desired treatment zone size of about 1 mm by 1 cm. In particular embodiments, laser diode bar 14 is configured to deliver about 1 J per treatment zone (again, based on a pulsed mode with a treatment zone of about 1 mm by 1 cm). For instance, in one example embodiments, the target peak output laser source power from a 1-cm wide laser diode bar is about 40 W at the target plane. For an example glide speed of about 4 cm/s, the pulse-on time for a 1-mm wide instantaneous treatment zone on the target plane is about 25 ms. This corresponds to about 1 J for a 1 mm by 1 cm treatment zone, or about 50 W and 1.25 J emitted by laser diode bar 14 assuming an example total optical efficiency of about 80%.

In some direct exposure embodiments, device 10 has an energy setting that can be optionally set to different values by a smart charging base accessory or on the device itself. Device 10 may include one or more types of sensors 26 for use in controlling the operation of the device, e.g., a skin contact sensor to detect contact with the skin, a dwell sensor to detect stationary positioning, a motion sensor to detect motion and/or speed of the device, and/or a displacement sensor configured to determine the distance (if any) that the device has moved across the skin. Any two or more of these sensors may be combined into a single sensor responsive to one or more than one parameter. Device 10 may include a single power button (mechanical or virtual) that the user activates to initiate the laser treatment. In one embodiment, once the application end of device 10 is in contact with skin and is not stationary on the skin (e.g., gliding or otherwise moving across the surface of the skin), device 10 enables the delivery of treatment laser energy (e.g., CW or pulsed radiation) as long as the power button is activated. The manual movement results in a generally random pattern of treatment zones 150 in the treated skin area, based on the manual movement of device 10 across the skin. The user can move device 10 across the skin at different speeds to help achieve the desired treatment comfort level. One or more sensors 26, e.g., a dwell sensor, displacement sensor, and/or motion sensor may be detect whether or not device 10 is moving, the speed of movement, and/or the distance device 10 has moved. Device 10 may utilize such detected data to prevent over-treatment of the same location on the skin.

Certain example direct exposure embodiments of device 10 are handheld, battery powered, compact skin treatment devices with all solid-state components (e.g., no mechanical motors) providing skin area coverage via manual motion (gliding or otherwise moving) modality and a CW or pulsed light source.

Eye Safety

Some embodiments of device 10 provide eye safe radiation, e.g., based on the divergence of beam(s) 94 emitted by laser diode bar(s) 14, by using diffusers or other optics, using an eye safety control system including one or more sensors 26, and/or by any other suitable manner. For example, in some embodiments or settings (including certain direct exposure embodiments and certain indirect exposure embodiments), device 10 meets the Class 1M or better (such as Class 1) eye safety classification per the IEC 60825-1, referred to herein as "Level 1 eye safety" for convenience. In other embodiments or settings (including certain direct exposure embodiments and certain indirect exposure embodiments), the device exceeds the relevant Maximum Permissible Exposure (MPE) (for 700-1050 nm wavelength radiation) or Accessible Emission Limit (AEL) (for 1400-1500 nm or 1800-2600 nm wavelength radiation) by less than 50%, referred to herein as "Level 2 eye safety" for convenience. In still other embodiments or settings (including certain direct exposure embodiments and certain indirect exposure embodiments), the device exceeds the relevant MPE (for 700-1050 nm wavelength radiation) or AEL (for 1400-1500 nm or 1800-2600 nm wavelength radiation) by less than 100%, referred to herein as "Level 3 eye safety" for convenience. Maximum Permissible Exposure (MPE) and Accessible Emission Limit (AEL) limits are discussed below, with respect to corresponding radiated wavelengths. In other embodiments or settings (including certain direct exposure embodiments and certain indirect exposure embodiments), device 10 meets the next highest eye safety classification after Class 1M per the IEC 60825-1, i.e., Class 3B, referred to herein as "Level 4 eye safety" for convenience.

Some embodiments of device 10 configured for direct exposure (and/or close proximity exposure) of laser radiation provide Level 4 eye safety as defined above; some direct exposure embodiments provide Level 3 eye safety as defined above; some direct exposure embodiments provide Level 2 eye safety as defined above; and some direct exposure embodiments provide Level 1 eye safety as defined above. Some embodiments of device 10 configured for indirect exposure (and/or close proximity exposure) of laser radiation provide Level 3 eye safety as defined above; some direct exposure embodiments provide Level 2 eye safety as defined above; and some direct exposure embodiments provide Level 1 eye safety as defined above.

Such levels of eye safety may be provided based on a combination of factors, including for example, one or more of the following: (a) the divergence of the beam(s), (b) the emitted power, (c) the wavelength of the emitted beam(s), (d) the arrangement of the laser diode bar(s), and in pulsed radiation embodiments or applications of device 10: (e) the pulse duration, and (f) the total energy per pulse. Thus, in some embodiments (including certain direct exposure, close proximity embodiments; certain direct exposure, remote proximity embodiments; certain indirect exposure, close proximity embodiments; and certain indirect exposure, remote proximity embodiments), one, some, or all of such factors may be selected or adjusted to provide Level 1, Level 2, Level 3, or Level 4 eye safety, as defined above.

The eye safety analysis under the IEC 60825-1 standard depends on the selected wavelength of laser radiation, as the standard defines different equations and limit values for different wavelength ranges. An eye safety analysis for the following two wavelength ranges is provided below: (a) 700-1050 nm wavelength radiation, and (b) 1400-1500 nm or 1800-2600 nm wavelength radiation.

(a) 700-1050 Nm Wavelength Radiation (e.g., for Hair Removal Treatments)

In the wavelength range below 1400-nm, retinal thermal hazard is the primary concern for eye safety. In the 700-1050 nm wavelength range (e.g., for providing certain hair removal treatments), to achieve a Class 1 eye-safe classification per IEC 60825-1 the Maximum Permissible Exposure (MPE) at the cornea from an extended source is given by the following formulas for pulsed (assuming a single pulse) and CW laser radiation (per Table A.2 in IEC 60825-1:2007), respectively:

$$MPE_{pulsed} = 1.8 \times 10^{-3} t^{0.75} C_4 C_6 \text{ J/cm}^2 \quad \text{Equation 3}$$

$$MPE_{CW} = 1.8 \times 10^{-3} C_4 C_6 C_7 T_2^{-0.25} \text{ W/cm}^2 \quad \text{Equation 4}$$

where $C_4 = 10^{0.002(\lambda - 700)}$, $\lambda$ is the wavelength in nm in the range of 700 to 1050 nm; $C_6 = 66.7$ for extended source with angular subtense greater than 100 mrad; $C_7 = 1$ in the same 700 to 1050 nm range; $T_2 = 100$ s. for the same large extended source. For a typical wavelength of 808-nm extended source used in certain hair removal applications, the corresponding MPEs in Equations 3 and 4 become $$MPE_{pulsed} = 10 \text{ mJ/cm}^2 \text{ or 20-ms pulse, or 117 mJ/cm}^2 \text{ for 500-ms pulse}$$

$$MPE_{CW} = 62 \text{ mW/cm}^2$$

To satisfy the IEC 60825-1 requirement of an eye-safe Class 1 laser, the measured fluence or irradiance onto a 7-mm circular aperture at a nominal distance of 10 cm from the device source output must be below the MPE calculated from Equation 3 or 4 for pulsed or CW radiation, respectively.

For certain dermatological treatments, e.g., hair removal, the skin fluence may be greater than 5 J/cm$^2$ for a pulsed laser. For a gliding CW laser moving at an example glide speed of 4 cm/s, the corresponding power density may be greater than 20 W/cm$^2$ to provide an effective treatment. However, these figures are significantly greater than the respective MPE limits shown above. Thus, in some embodiments, the radiation from the laser diode bar(s) may be attenuated in order to achieve the MPE limits. For example, the source laser radiation may be attenuated by (a) divergence of the radiation from the laser diode bar(s), (b) introducing a diffuser or other divergent optic downstream of from the laser diode bar(s), and/or (c) any other suitable technique. The attenuation may be defined by an attenuation factor "A" wherein A=fluence emitted from the laser diode bar(s)/fluence received at a nominal eye accommodation distance of 10 cm as specified in the IEC standard.

For the example fluence values listed above (5 J/cm$^2$ for a pulsed laser radiation and 20 W/cm$^2$ for CW laser radiation), the required attenuation factor A to achieve the respective MPE limit above is: A≈43 for a 500-ms pulse with a fluence of 5 J/cm$^2$ (i.e., 5 J/cm$^2$/0.117 J/cm$^2$); A≈500 for a 20-ms pulse with a fluence of 5 J/cm$^2$ (i.e., 5 J/cm$^2$/0.010 J/cm$^2$); and A≈322 (i.e., 20 J/cm$^2$/0.062 J/cm$^2$).

For direct radiation (i.e., no optics downstream of the laser source), an attenuation factor $A_{direct}$ relative to the source can be estimated at the classification measurement distance of 10 cm for a simple direct divergent source. It is derived similar to Equation 2 and is given by for a 7-mm circular test aperture:

$$A_{direct}=2.1\times10^3 \tan(\Phi_F/2)\tan(\Phi_S/2) \quad \text{Equation 5}$$

where $\Phi_F$ and $\Phi_S$ are the beam divergence angles in the fast and the slow axis, respectively. For a laser diode bar providing a fast-axis divergence of about 40° and slow-axis divergence of about 10°, this attenuation factor $A_{direct}$ is about 67. Thus, based on the MPE limits listed above (10 mJ/cm² for 20-ms pulse, 117 mJ/cm² for 500-ms pulse, or 62 mW/cm² for CW radiation), the divergence of radiation from such laser diode bar (assuming no additional attenuating factors, e.g., a diffuser) provides Class 1 eye safety only for certain radiation pulse conditions, and not for CW radiation.

However, adding a diffuser to the laser diode bar output that provided a Lambertian angular distribution of the source radiation may increase the intrinsic eye safety of the device. For a Lambertian diffuser, the attenuation factor $A_{Lambertian}$ is given by:

$$A_{Lambertian}=(10 \text{ cm}/0.35 \text{ cm})^2=816 \quad \text{Equation 6}$$

wherein 10 cm is the target test distance, and 0.35 cm is the prescribed test aperture radius at the target, such that Equation 6 follows the inverse square law.

Thus, certain embodiments may utilize a Lambertian or substantially Lambertian diffuser to achieve a desired intrinsic eye safety (e.g., Level 4, Level 3, Level 2, or Level 1 eye safety), even for CW radiation. For example, diffuser 64 shown in FIG. 2 may be a Lambertian or substantially Lambertian diffuser. Some embodiments may incorporate a diffuser having properties described in U.S. Pat. No. 7,250,045, U.S. Pat. No. 7,452,356, or US Patent Application Publication No. US 2006/0009749, all three of which disclosures are hereby incorporated by reference in their entirety.

Table 1 below provides several examples of device configurations and settings for achieving intrinsic eye safety with Class 1 or 1M classification, for radiation in the 700-1050 nm wavelength range (e.g., for laser hair removal treatments).

TABLE 1

| Parameter | Example Values | Example Embodiment | Example Values | Example Embodiment |
|---|---|---|---|---|
| Configuration | direct exposure (no optics) | direct exposure (no optics) | direct exposure (with diffuser) | direct exposure (with diffuser) |
| Radiation source | Laser diode bar | Laser diode bar | Laser diode bar | Laser diode bar |
| Radiation mode | Pulsed | Pulsed | CW | CW |
| wavelength | 700-1050 nm | 808 nm | 700-1050 nm | 808 nm |
| beam divergence at skin surface (fast axis, slow axis) | 35°-45° fast axis 6°-12° slow axis | 45° fast axis 10° slow axis | Lambertian | Lambertian |
| Pulse duration (ms) | 100-500 | 250 | CW | CW |
| Power (W/cm²) | 20-60 | 20 | 20-80 | 50 |
| Emitted Fluence (J/cm²) | 2-30 | 5 | | |
| MPE | 35-117 mJ/cm² | 70 mJ/cm² | 62 mW/cm² | 62 mW/cm² |
| MPE required attenuation factor, $A_{MPE}$ | 40-140 | 72 | 300-1300 | 806 |
| Attenuation factor, $A_{source}$ | 35-90 | 76 | 816 | 816 |
| Exposure at test distance (10 cm) | 22-857 mJ/cm² | 66 mJ/cm² | 25-98 mW/cm² | 61 mW/cm² |
| Eye safety classification | Class 1M for $A_{source} > A_{MPE}$ | Class 1M | Class 1 for $A_{source} > A_{MPE}$ | Class 1 |

(b) 1400-1500 Nm or 1800-2600 Nm Wavelength Radiation (e.g., for Fractional Treatments)

In the wavelength ranges of 1400-1500 nm and 1800-2600 nm (e.g., for providing certain fractional treatments), corneal damage is typically the primary concern for eye safety. In some embodiments that radiate in such wavelength ranges, the beam divergence inherently provided by the laser diode bar(s), alone or in combination with other eye safety features, may provide a desired eye safety for device 10. For example, the beam divergence from a typical laser diode bar (alone or in combination with other eye safety features) may provide Level 1, Level 2, Level 3, or Level 4 eye safety, depending on the other selected parameters. An analysis of relevant issues is discussed below.

A highly divergent intense light source may provide eye safe radiation. For certain wavelengths greater than 1400 nm (including, e.g., typical wavelengths used in fractional laser treatment), the light source is greatly attenuated by the water absorption in the eye anterior chamber. Thus, there is substantially little or no retinal hazard in this wavelength range. The emission limit is determined by the potential corneal damage. In particular, the damage threshold is determined by the maximum irradiance exposure of each localized emitter source. The focusing effect of eye's cornea and lens is not relevant in this wavelength range (above 1400 nm) and thus does not contribute to eye hazard in this wavelength range. Thus, for this wavelength range (above 1400 nm), the eye safety analysis for a laser diode bar is essentially the same as the analysis of each individual emitter of the laser diode bar. For Class 1M eye safety classification per IEC 60825-1, the Accessible Emission Limit (AEL) in the wavelength range of 1400 to 1500 nm and 1800 to 2600 nm is described by a simple equation in Table 4 of IEC 60825-1:2007:

$$AEL=4.4t^{0.25} \text{ mJ} \quad \text{Equation 1}$$

AEL energy is measured at 70 mm from the source with a circular aperture of 7 mm in diameter (Condition 2 measurement setup described in Table 11 of IEC 60825-1:2007, applicable for diverging beam). In this equation, t (in unit of seconds) is the source pulse duration in the range of 1 ms to 350 ms. For a laser diode bar, this pulse duration may be in the range of 1 to 10 ms. Therefore, the corresponding AEL is 0.8 to 1.4 mJ.

The actual source AE (Accessible Energy) can be estimated for a given beam divergent characteristics. It can also be measured experimentally with the appropriate aperture stop (7-mm wide) and measurement distance (70-mm from the source). The AE at a distance 70-mm from the treatment aperture is given by (this is approximately correct for a Gaussian beam from a diffraction limited laser):

$$AE=2.5\times10^{-3}Q/[\tan(\Phi_F/2)\tan(\Phi_S/2)]\text{mJ} \quad \text{Equation 2}$$

where Q (in unit of mJ) is the source energy at the treatment plane, and $\Phi_F$ and $\Phi_S$ are the beam divergence in the fast and slow axis, respectively. To achieve the Class 1M eye safety classification, AE must be lower than the AEL for the corresponding pulse duration.

Table 2 below provides example configurations and device settings for providing Level 1 eye safety (Class 1M or better per standard IEC 60825-1) for example embodiments providing pulsed radiation in the 1400-1500 nm or 1800-2600 nm wavelength ranges (e.g., for fractional treatment).

TABLE 2

| Parameter | Example Values | Example Embodiment |
|---|---|---|
| Configuration | direct exposure (no optics) | direct exposure (no optics) |
| Radiation source | Laser diode bar | Laser diode bar |
| Number of emitters | 10-30 | 20 |
| Radiation mode | Pulsed | Pulsed |
| wavelength | 1400-1500 nm or 1800-2600 nm | 1400-1500 nm or 1800-2600 nm |
| beam divergence at skin surface (fast axis, slow axis) | 35°-45° fast axis, 6°-12° slow axis | 45° fast axis 10° slow axis |
| Pulse duration (ms) | 5-20 | about 10 |
| Total bar power (W) | 10-40 | about 20 |
| Total bar energy per pulse (mJ) | 50-800 | about 200 |
| Emitter power (W) | 0.3-4 | about 1 |
| Emitter energy per pulse (mJ) | 2-80 | about 10 |
| AEL (mJ) | 1.2-1.7 | about 1.4 |
| AE (mJ) | 0.1-12 | about 0.7 |
| Eye safety classification | Class 1M for AE < AEL | Class 1M |

Because certain embodiments or device settings—for any of example wavelength ranges of 700-1050 nm, 1400-1500 nm, and 1800-2600 nm—may provide Level 1, Level 2, Level 3, or Level 4 eye safety based on the appropriate selection of parameters discussed above, in some such embodiments an eye safety sensor or system may be omitted. However, some embodiments, even those providing Level 1 eye safety, may include an eye safety sensor or system to provide redundancy, to meet particular regulatory standards, or for other reasons.

In at least some embodiments additional eye safety is provided by incorporating a contact sensor that enables pulsing the laser only when in contact with the skin. Thus, in such embodiments, the likelihood of retinal and/or corneal eye injury may be reduced or substantially eliminated unless the device is literally pressed to the eye surface.

Some embodiments may include an optical diffuser (e.g., as discussed above), one or more optics (e.g., a lens), or other elements and configurations (e.g., selected pulse durations, wavelengths, pulse repetition frequencies, beam profile characteristics, and beam propagation characteristics) to provide increased eye safety. Other embodiments may provide a particular eye safety level (e.g., Level 1, Level 2, Level 3, or Level 4 as defined above) without such elements, and in a direct exposure configuration (and/or close proximity configuration), due to the inherent or selected divergence of the laser diode bar combined with suitable operational parameters of the beam source, e.g., as discussed above.

Figure 9:
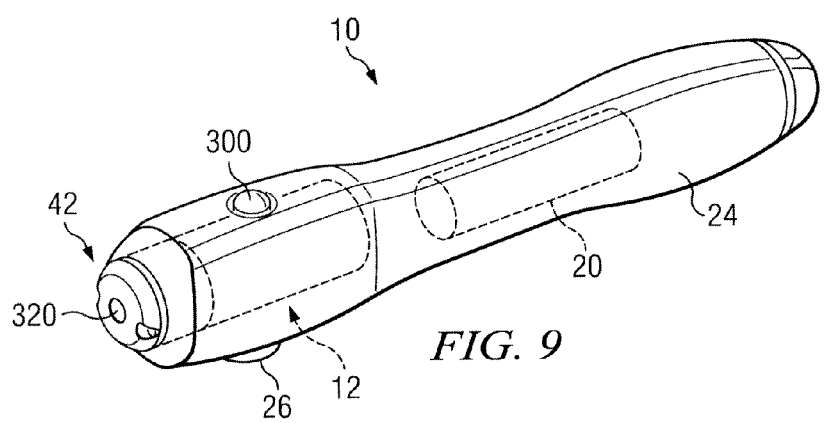
FIG. 9 illustrates an example treatment device including a laser diode bar and configured as a direct exposure device, according to example embodiments of the present disclosure.

FIG. 9 illustrates an example treatment device 10 including a laser diode bar 14 (high fill-factor or low fill-factor) and configured as a direct exposure device, according to example embodiments of the present disclosure. The example device includes a laser engine 12 including a laser diode bars 14 and one or more batteries 20 within a device housing 24. In some embodiments, the battery or batteries 20 may be provided in the laser engine 12. Battery or batteries 20 may include any number and type of batteries, e.g., AA-sized or smaller batteries, or rechargeable or non-rechargeable cells (e.g., Li ion cells), or any other type of battery.

Device 10 has an application end 42 configured to contact the user's skin as device 10 is moved across the skin during a treatment session. In this embodiment, application end 42 is defined by a leading end of laser engine 12, which projects from device housing 24. The application end 42 may include a laser treatment aperture 320 through which a laser beam 96 generated by the laser engine 12 is delivered to the user.

In addition, as discussed above, one or more sensors 26, e.g., a skin contact sensor, a dwell sensor, a motion sensor, and/or a displacement sensor may be located on device 10, e.g., at application end 42. In some embodiments, such sensors may include, e.g., any of the various sensors disclosed in U.S. Ser. No. 13/366,246 (e.g., one or more skin-contact sensor 104, dwell sensor 116, motion/speed sensor 102, and/or displacement sensor 100A, 100B, 100C, or 100D). In some embodiments, device 10 includes a skin contact sensor and a dwell sensor configured to avoid unintentional exposure and/or overexposure of the skin (e.g., by preventing stacking or overlapping of treatment zones 150). The skin contact sensor and dwell sensor may be provided by a single combined contact/dwell sensor, or may be provided as separate sensors. In either alternative, the sensor(s) may be optical or capacitance based or use other suitable means. Contact with the skin may be detected by analyzing an amplitude of an optical reflectance or capacitance signal generated by the sensor. Further, dwelling of device 10 on the skin may be detected by analyzing signal in the optical reflectance or capacitance signal associated with application end 42 of device 10 moving across the skin or by other suitable means. Because skin surface is not perfectly smooth and the manual moving of a device cannot achieve perfect steady motion, stiction (static friction) between device 10 and skin and/or other physical principles result in micro-displacement between the sensor and the skin surface. For example, a capacitive sensor's signal is inversely proportional to the relative displacement between the sensor and the test surface. Any micro-displacement due to stick-and-slip manual movement will result in a translational signal on top of the nominal steady-state sensor signal. This signal may be analyzed to determine whether device 10 is moving across the skin, or dwelling at the same location. Such analysis may include any suitable algorithms, e.g., comparing the signal to one or more threshold values.

In the example shown in FIG. 9, device 10 includes a power button 300. Device 10 enables the delivery of beams to the skin in a pulsed manner when power button 300 is depressed by the user, and the sensor(s) 26 detect that device 10 is in proper contact with the skin and moving across the skin (i.e., not dwelling on the skin).

The specific user interface scheme, and the shape and size of device 10 housing may be selected as desired. In some embodiments, the shape and size of device 10 housing is easy to grip and includes a simple, conveniently located power button 300 and/or other user interfaces. In addition, the shape of device 10 may be ergonomic, and/or be configured to provide good visibility of the target area 40.

Embodiments with Beam Scanning System

Certain indirect exposure embodiments include an automated beam-scanning system that repeatedly scans a beam generated by laser diode bar 14 to provide a time-sequential series of output beams that are delivered to the skin, the series of output beams being offset (angularly and/or translationally) from each other such that a row or array of treatment zones are generated on the skin for each scan of the beam-scanning system (e.g., each revolution of a rotating multi-faceted scanning element). Device 10 may be glided across the target area 40 in a direction generally transverse to the direction of scanning provided by the beam-scanning system, such that the combination of the manual gliding and automated beam scanning results in a two-dimensional array of treatment zones generated on the skin for each glide of the device across the skin.

Figure 10:
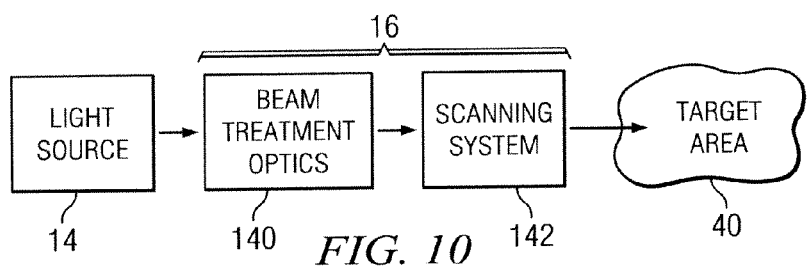
FIG. 10 illustrates aspects of an example treatment device including a laser diode bar and a beam-scanning system, according to certain embodiments.

FIG. 10 illustrates aspects of an example treatment device 10 including laser diode bar(s) 14 and a beam-scanning system, according to certain embodiments. In such embodiments, optics 16 may include beam treatment optics 140 and a scanning system 142. Beam treatment optics 140 may include any one or more optical elements, such as lenses, mirrors, and other reflective and/or fully or partially transmissive elements, for controlling one or more optical parameters of the radiation generated by laser diode bar(s) 14, such as the direction, shape (e.g., convergent, divergent, or collimated), and/or intensity profile of the radiation.

Scanning system 142 may be configured to scan an individual light beam (or multiple individual light beams) generated by laser diode bar(s) 14 into a sequentially-delivered array of beams to create a pattern of treatment zones 150 (e.g., spots, lines, or other shapes) in the target area 40.

Figure 11:
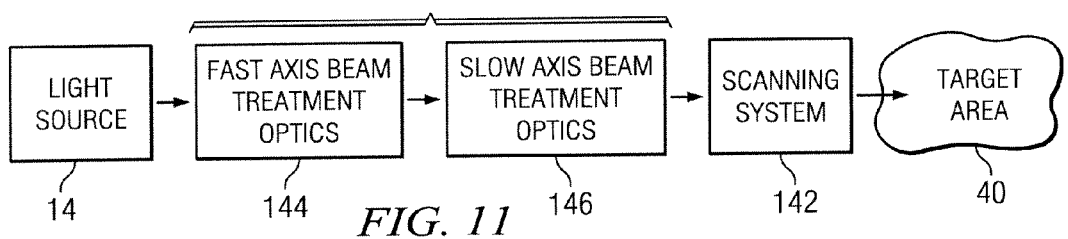
FIG. 11 illustrates example aspects of the beam treatment optics of a treatment device, according to certain embodiments.

FIG. 11 illustrates example aspects of the beam treatment optics 140 of a treatment device 10, according to certain embodiments. Beam treatment optics 140 may include axis-asymmetric elements that act on different optical axes of an incident light beam differently. For example, beam treatment optics 140 may include first optics configured to influence an incident light beam primarily in a first optical axis, and second optics configured to influence the light beam in a second optical axis orthogonal to the first axis. Influencing the beam along a particular optical axis may include affecting the intensity profile of the beam along the particular optical axis. As used herein, the intensity profile of the beam along a particular optical axis refers to the shape of the intensity profile along the particular optical axis (e.g., Gaussian, flat-topped, etc.); whether the beam is converging, diverging, or collimated; the degree of convergence or divergence of the beam; etc.

Thus, in the example embodiment shown in FIG. 11, beam treatment optics 140 include separate fast axis beam treatment optics 144 (or fast axis optics 144) and slow axis beam treatment optics 146 (or slow axis optics 146). Fast axis optics 144 include one or more optical elements configured to affect the intensity profile of the beam in the fast axis, while slow axis optics 146 include one or more optical elements configured to affect the intensity profile of the beam in the slow axis. In certain embodiments, fast axis optics 144 are configured to affect the fast axis intensity profile without substantially affecting the slow axis intensity profile. Further, in certain embodiments, slow axis optics 146 are configured to affect the slow axis intensity profile without substantially affecting the fast axis intensity profile. In particular embodiments, both of these features are provided: fast axis optics 144 affect the fast axis intensity profile without substantially affecting the slow axis intensity profile, and slow axis optics 146 affect the slow axis intensity profile without substantially affecting the fast axis intensity profile.

Alternatively, fast axis optics 144 and slow axis optics 146 may be partially or fully integrated. For example, a particular optical element (e.g., mirror or lens) may affect both the fast axis and slow axis intensity profiles. Such element may be referred to as a multi-axis optical element, and may or may not be symmetrical about all axes (e.g. spherical). Some embodiments may include one or more multi-axis optical elements, along with one or more separate fast axis optical elements; or one or more multi-axis optical elements, along with one or more separate slow axis optical elements; one or more multi-axis optical elements, along with one or more separate slow axis optical elements and one or more separate fast axis optical elements; or any other combination thereof.

Further, each of fast axis optics 144 and slow axis optics 146 may be separate from, or integral with, scanning system 142. In other words, scanning system 142 may influence either one, both, or neither of the fast axis and slow axis intensity profiles. Thus, for example, scanning system 142 may provide fast axis optics 144, with slow axis optics 146 being provided separately. Alternatively, scanning system 142 may provide slow axis optics 146, with fast axis optics 144 being provided separately. Alternatively, scanning system 142 may provide both fast axis optics 144 and slow axis optics 146. In the example embodiment shown in FIGS. 11A-11B, slow axis optics 146 are provided by scanning system 142, while fast axis optics 144 are provided separately.

The term "optics" (e.g., as used in beam treatment optics 140, fast axis beam treatment optics 144, and slow axis beam treatment optics 146) may include a single optical element or multiple optical elements. In some embodiments, device 10 includes only a single fast axis optical element and a single slow axis optical element.

Figure 12A:
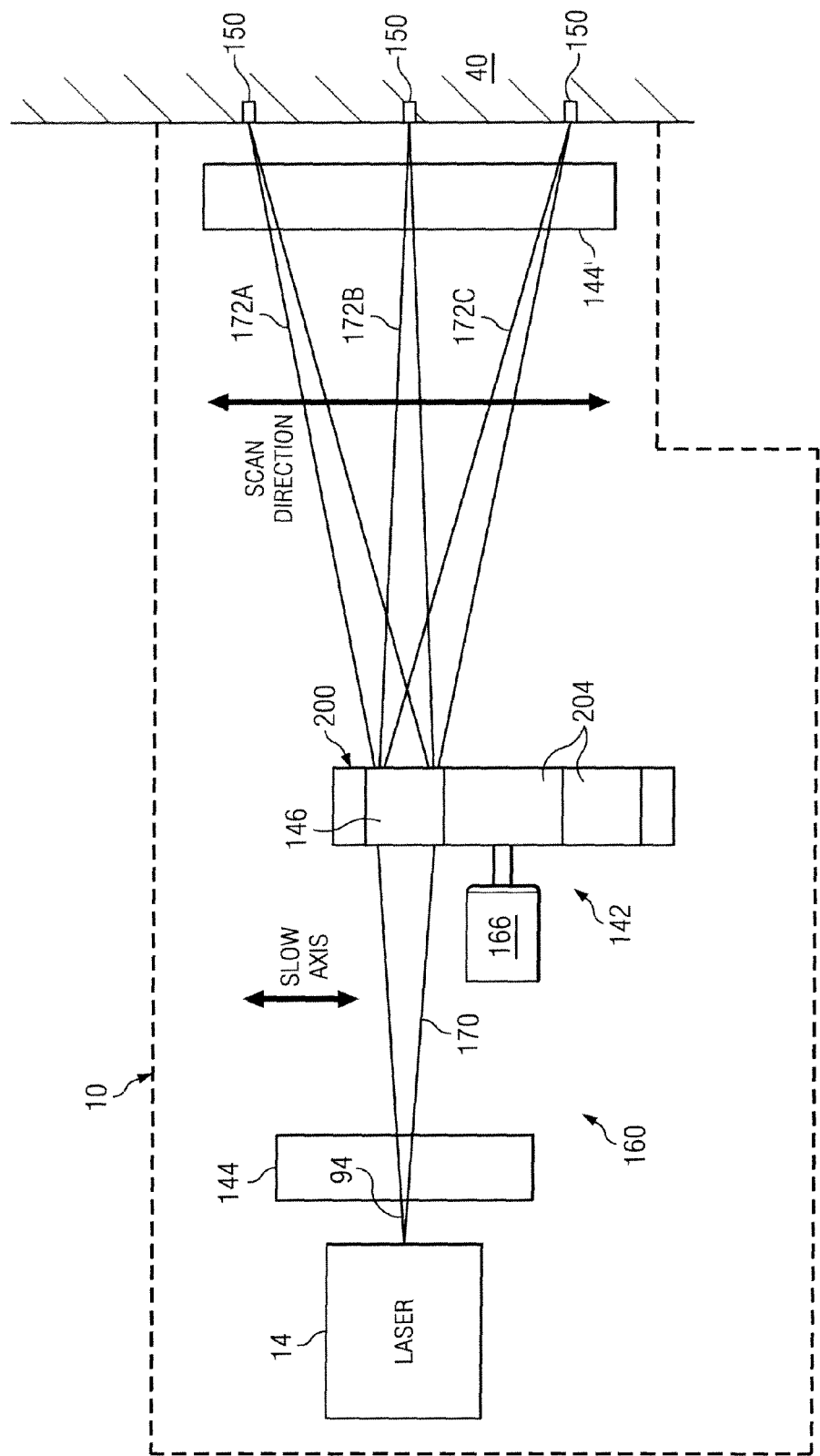
FIGS. 12A and 12B illustrate top and side views, respectively, of a beam delivery system that includes a rotating scanning element, according to certain embodiments.
Figure 12B:
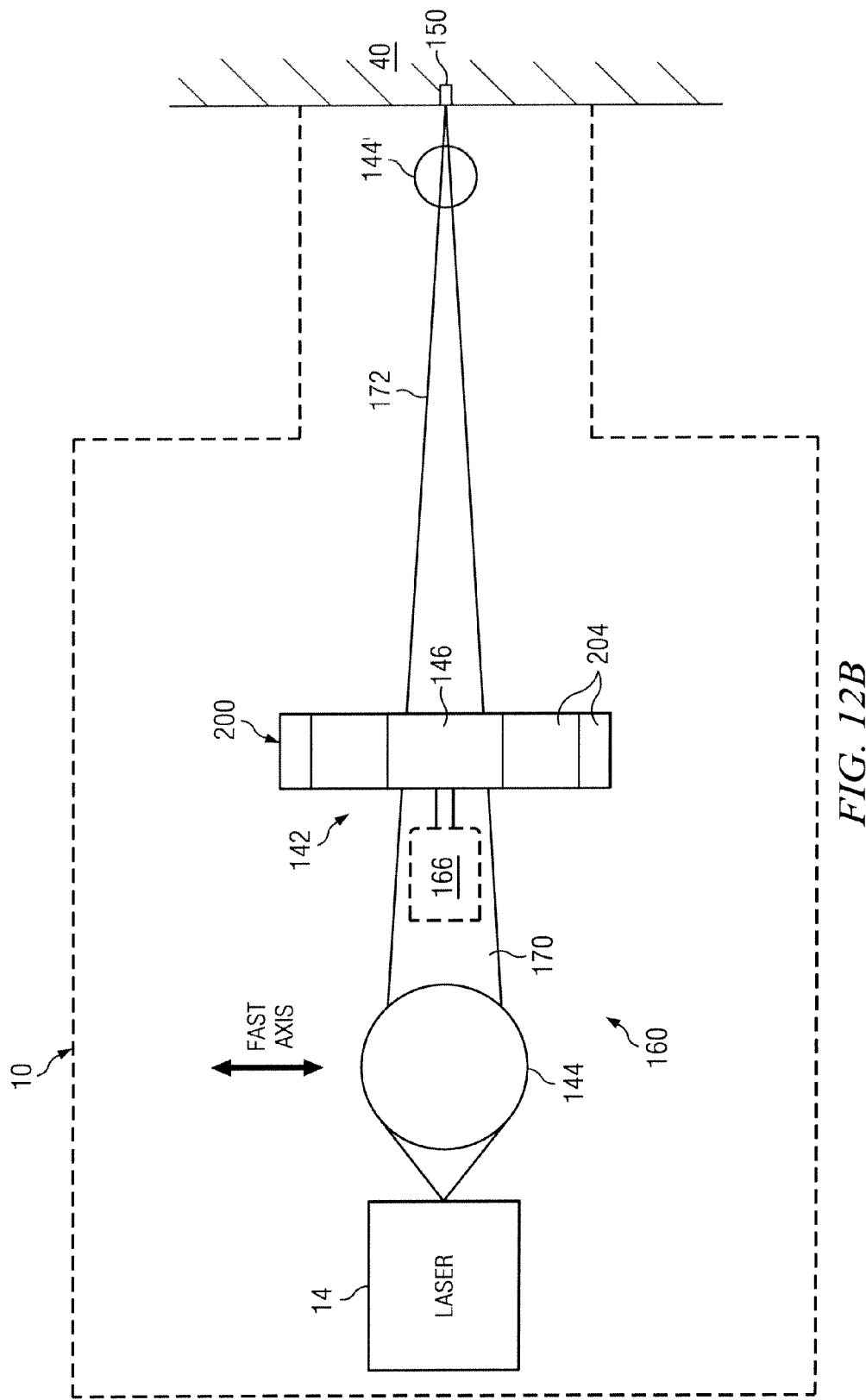

FIGS. 12A and 12B illustrate top and side views, respectively, of a beam delivery system 160 that includes a rotating scanning element 200, according to certain embodiments. Beam delivery system 160 includes a laser diode bar 14 that generates a beam, and optics 16 which control and scan the beam to a target area 40 to form a pattern of treatment zones 150. Optics 16 may include a fast axis optic 144, and a scanning system 142 that includes a scanning element 200 rotated by a motor 166. In some embodiments, optics 16 may also include a downstream fast axis optic 144', e.g., to refocus the fast-axis profile from a dual-beamlet profile to a single-beam profile. In other embodiments, the downstream fast axis optic 144' is omitted.

Fast axis optic 144, e.g., a rod lens, aspheric lens, or any other suitable optical element, is configured to convert the beam in the fast axis from rapidly diverging to less diverging (e.g., slowly diverging, collimated, or converging) toward target area 40, as shown in FIG. 11B. In some embodiments, fast axis lens 64 does not influence the slow axis beam angular distribution profile (e.g., the convergence/divergence of the slow axis), as shown in FIG. 12A.

Fast axis optic 144 delivers an input beam 170 to rotating scanning element 200, which includes multiple lenslets 164 that generate a successive series of output beam 172 toward target area 40, as shown in FIG. 12A. In addition to deflecting the various output beams in the scan direction to form a desired pattern of treatment zones in the target area 40, lenslets 164 of element 200 also convert the beam in the slow axis from slowly diverging to slowly converging. Thus, a single element 200 operates as both the beam scanning element and the slow axis optic 146, thus reducing or minimizing the number of separate components for such functions, which may be desirable. In some embodiments, lenslets 164 of element 200 do not influence the fast axis beam angular distribution profile (e.g., the convergence/divergence of the fast axis), as shown in FIG. 12B.

Fast axis optic 144 and lenslets 164 of element 200 may be configured to converge the beam in the fast and slow axes, respectively, such that each output beam 172 has a focal point or focal plane located at or slightly above the surface of the skin, in some embodiments. Further, as discussed above, in some embodiments a downstream fast axis optic 144' is provided for additional focusing and/or imaging and/or treatment of output beams 172.

Operation of Scanning System

In some embodiments, device 10 may be configured to be used in a "stamping mode" in which device 10 is held relatively stationary at different locations on the skin, with one or more scanned rows or arrays of treatment zones (overlapping or not overlapping) delivered at each location of device 10. Thus, device 10 may be positioned at a first location, one or more scanned rows or arrays of treatment zones may then be delivered to the skin while device 10 is held relatively stationary, device 10 may then be moved—by lifting device 10 and repositioning it or by gliding device 10 across the surface of the skin—to a new location, one or more scanned rows or arrays of treatment zones may then be delivered at that location, and so on, in order to cover a target area 40 as desired.

Figure 13A:
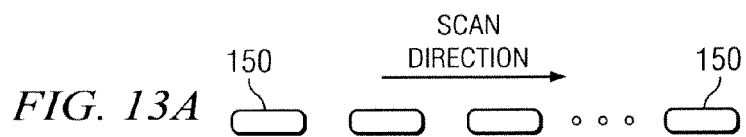
FIGS. 13A and 13B illustrates example patterns of treatment zones delivered by one scan of a light beam by a device including a beam scanning system, in a stationary mode (e.g., stamping mode) of the device, illustrating example patterns resulting from different treatment zone widths or lateral spacing between treatment zones.
Figure 13B:
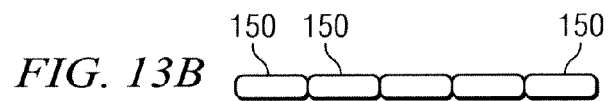

FIGS. 13A and 13B illustrates example patterns of treatment zones 150 delivered by one scan of a light beam by beam scanning system 142, with device 10 held stationary at one location on the skin (e.g., during operation in a stamping mode), illustrating example patterns resulting from different treatment zone widths or lateral spacing between treatment zones.

In particular, FIG. 13A illustrates an example pattern in which treatment zones 150 are spaced apart in the scan direction, while FIG. 13B illustrates an example pattern in which treatment zones 150 are aligned end-to-end in the scan direction, to form an extended line. The relative spacing between treatment zones 150 may be selected as a factor of the design and dimensions of the laser diode bar 14, the design of scanning system 142 (e.g., the design and/or orientation of deflection sectors 104 of scanning element 200), the proximity gap spacing, etc.

Further, although FIGS. 13A and 13B show the elongated direction of treatment zones 150 aligned with the scan direction, the elongated direction of treatment zones 150 may be perpendicular to the scan direction or otherwise aligned relative to the scan direction, e.g., by rotating laser engine 12 (e.g., 90 degrees) relative to the device housing 24.

In other embodiments, as discussed above, device 10 may be configured to be used in a "gliding mode," in which the device is manually dragged or glided across the skin while delivering scanned radiation to the target area 40. Scanning system 142 may repeatedly scan rows of treatment zones onto the target area 40 as device 10 is glided across the skin, thus producing a generally two-dimensional array of treatment zones in the target area 40.

Figure 14:
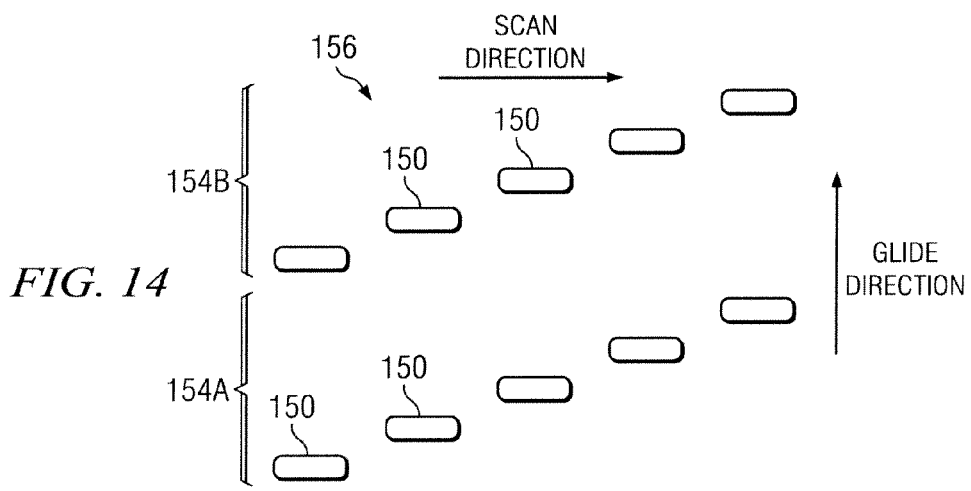
FIG. 14 illustrates an example pattern of treatment zones delivered by three scans of a light beam by a device including a beam scanning system, in a manual gliding mode of the device.

FIG. 14 illustrates an example array of treatment zones 150 delivered by two scans of a light beam by a device including a beam scanning system, in a manual gliding mode of the device. In particular, the figure shows two scanned rows of treatment zones 150, indicated as rows 154A and 154B, aligned in the glide direction, which forms a two-dimensional array 156 of treatment zones 150. Each row 154 is generally aligned diagonal with respect to the scan direction due to the movement of the device in the glide direction during the successive delivery of individual treatment zones 150 in each row 154.

The degree to which each row is aligned diagonal with respect to the scan direction, which may influence the spacing of adjacent treatment zones aligned in the glide direction, is a factor of multiple variables, including the glide speed (i.e., the speed at which device 10 is glided across the skin) and the scanning rate (i.e., the rate at which treatment zones are successively delivered to the skin and the time between scans. In some embodiments, the scanning rate or particular aspects of the scanning rate (e.g., pulse on time, pulse off time, pulse frequency, etc.) may be selectable or adjustable automatically by control system 18, manually by a user, or both.

Further, the distance between adjacent treatment zones in the scan direction is a factor of multiple variables, including the scanning rate, distance between the center points of adjacent treatment zones, and the size and shape of individual treatment zones, which variables may be defined by the configuration of the optics of scanning system 142 or other factors. In some embodiments, one or both of these variables may be selectable or adjustable automatically by control system 18, manually by a user, or both. In some embodiments or device settings, adjacent treatment zones in the scan direction are spaced apart from each other, thus providing fractional treatment. In some embodiments or device settings, adjacent treatment zones in the scan direction may abut each other edge-to-edge, or may overlap each other, in order to provide contiguous rows of irradiated areas. Such contiguous rows may be spaced apart from each other in the glide direction, may abut each other edge-to-edge, or may overlap each other to provide a fully covered (i.e., non-fractional) irradiated area, as defined by a variety of factors such as those discussed above, which may or may not be manually and/or automatically selectable or adjustable.

Thus, it should be clear that the fractional pattern of treatment zones shown in FIG. 14, in which treatment zones are spaced apart from each other in both the glide direction and scan direction, is merely one example pattern. Device 10, and in particular scanning system 142, may be configured to provide a wide variety of treatment zone patterns.

Scanning system 142 may include any suitable optics and other elements for scanning an individual light beam into a sequentially-delivered array of beams to form a pattern of treatment zones in the target area 40. For example, as discussed below, scanning system 142 may include a rotating element having a number of deflection sectors that successively deflect (e.g., reflect or transmit with a deflection) a single incident light beam to provide an array of successively delivered output beams. In some embodiments, the rotating element may be generally disc-shaped, or generally cup-shaped, for example. The deflection sectors may be arranged around a circumference of the rotating element and may be configured to successively deflect the incident light beam by different angles to provide a successive array of deflected output beams. This array of deflected output beams may be delivered directly to the target area 40, or may be influenced by further optics before being delivered to the target area 40. For example, optics may be provided to parallelize the array of deflected beams before being delivered to the target area 40.

The example embodiments discussed above include devices configured for gliding mode, and devices configured for stamping mode. In some embodiments, device 10 may be configured for use in both a gliding mode and stamping mode, as selected by the user, for example.

Figure 15:
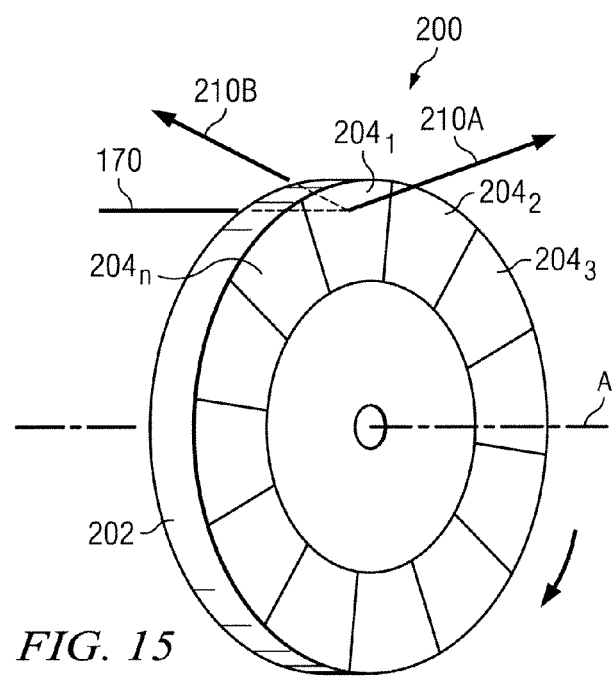
FIG. 15 illustrates a basic structure of an example rotating element for a beam-scanning system, according to some embodiments.

FIG. 15 illustrates a basic structure of rotating element 200, according to some embodiments. Element 200 has a body 202 configured to rotate about an axis A. Body 202 includes a plurality of sectors 204 generally arranged around the circumference or periphery of the body 202 and configured to deflect an input beam 170 into an array of output beams 172 offset from each other. Depending on the particular embodiment, each sector 204 may transmit but deflect the input beam 170, as indicated by example arrow 210A (e.g., a transmissive element) or reflect the input beam, as indicated by example arrow 210B (e.g., a reflective element). As each individual sector 204 rotates through the input beam 170, the deflection of the corresponding output beam 172 may remain constant or near constant so that each output beam 172 is stationary or near stationary with respect to device 10. Alternatively, the deflection of each output beam 172 may vary during the rotation of the corresponding sector 204 through the input beam 170 so that each output beam 172 traces a pattern, such as a line or arc.

Also, in addition to deflecting an input beam 170 to generate an array of offset output beams 172 (e.g., offset along a scan direction), each sector 204 may further influence the input beam 170 in one or more axis. For example, each sector 204 may further influence the input beam 170 by having curvature in its reflection surface that provides optical power, similar to the examples provided above for the transmissive disk or cup shaped scanning elements. For example, in addition to the deflection, each sector 204 may further act as a slow axis optic and/or a fast axis optic. In some embodiments, each sector 204 may deflect the input beam 170 in the slow axis direction, and also influence the convergence/divergence of the input beam 170. For example, element 200 may receive an input beam 170 that is diverging in the slow axis direction, and each sector 204 may both (a) deflect the input beam 170 by a particular degree, and (b) convert the diverging beam into a collimated or converging beam, e.g., such that individual collimated, focused, or pseudo-focused output beams 172 can be delivered to the target area, for generating treatment zones.

In addition to the various aspects of element 200 and sectors 204 discussed above, in some embodiments, individual sectors 204 may be configured to produce output beams 172 having a constant angular deflection as that sector 204 rotates through the input beam 170.

Each sector 204 (or least some of the sectors 204) may be a "constant angular deflection" sector, which is defined a sector that deflects the input beam 170 such that the angular deflection of the output beam 172 relative to the input beam 170 remains substantially constant as that sector 204 rotates through the input beam 170. In other words, the angular direction of each output beam 172 remains substantially constant relative to the input beam 170 (and relative to the structure of device 10) during the time that each corresponding sector 204 rotates through the input beam 170. Some elements 200 generate an array of constant angular deflection output beams 172 that propagate at constant angles that are different from each other.

Thus, with constant angular deflection sectors 204, if device 10 is held stationary relative to the user's skin, each output beam 172 will substantially dwell at a particular point on target area 40 until the next successive sector 204 rotates into the path of the input beam 170, at which time the beam "jumps" to a new location corresponding to the next successive output beam 172. Thus, if device 10 is held stationary relative to the user's skin, constant angular deflection sectors 204 provide substantially stationary treatment zones on the skin.

However, as discussed above, in at least some embodiments or operational modes, device 10 is designed to be glided across the surface of the skin during operation, in a manner similar to a shaver being glided across the skin. Thus, in a system with constant angular deflection sectors 204, each output beam 172 moves relative to the skin as device 10 glides across the skin, such that each treatment zone moves relative to the skin, resulting in elongation, "smearing," or "blurring" in the direction of the gliding. However, despite this smearing of individual treatment zones, sufficient thermal energy may be provided to the treatment zones on a delivered energy per volume basis to provide the desired affect in the target area 40, at least within a range of operating parameters. For example, the desired effect may be provided as long as the device 10 is not glided across the skin extremely rapidly. Further, some amount of smearing may actually be beneficial for achieving a desired level of delivered energy per volume of irradiated or affected tissue, as a function of selected design and/or operational parameters (e.g., treatment zone size and/or shape, beam intensity, fluence, and/or intensity profile of the delivered output beams, pulse duration and/or frequency, rotational speed of rotating element 200, etc.). Thus, in certain embodiments, "constant angular deflection" sectors may be used to achieve the desired treatment effects.

In some embodiments, smearing caused by gliding may be compensated for, either partially or entirely. For example, the sectors 204 may be configured to be (a) substantially stationary in the non-glide direction (for which there is no smearing) and (b) to move the beam in the glide direction (for which there is normally smearing) at the same rate or nearly the same rate as the gliding, thereby compensating or partially compensating for smearing. In these embodiments, a glide rate sensor may provide feedback to the user or the device to ensure that the gliding rate is within predefined ranges such that the smearing compensation is effective.

Some Example Embodiments and Example Operation Parameters

Any of the various features and configurations discussed herein may be combined in any suitable manner, for providing a variety of different treatments. Some example configurations with example parameter values are provided below. It should be understood that these are examples only.

1. Direct exposure embodiment with high fill-factor laser diode bar, operating in a gliding mode in which the device is glided perpendicular to the elongated direction of the laser diode bar, with continuous wave (CW) radiation, e.g., for treatments such as hair removal and skin tightening.

| Parameter | Example values | Specific example |
| --- | --- | --- |
| Laser diode bar | | |
| fill factor | 50%-90% | about 70% |
| number of emitters | 49-89 | 69 |
| emitter width $W_E$ | 90-150 μm | 100 μm |
| emitter spacing $W_S$ | 10-100 μm | 40 μm |
| Total optical efficiency (laser diode bar to target) | 70%-90% | about 80% |
| Proximity gap spacing | 1 mm-10 mm | about 1.5-2.5 mm |
| Power emitted | | |
| per emitter | 0.25-0.8 W | 0.6 W |
| total emitted by diode bar | 20-40 W | 40 W |
| Length of instantaneous irradiated area on target (perpendicular to elongated direction of diode bar) | 0.5-3 mm | 1 mm |
| Glide speed | 2-6 cm/s | 4 cm/s |
| Point dwell time (irradiation time at random point near center of treatment zone) | 10-150 ms | 25 ms |

2. Direct exposure embodiment with high fill-factor laser diode bar, operating in a gliding mode in which the device is glided perpendicular to the elongated direction of the laser diode bar, with pulsed radiation for fractional treatment, e.g., for anti-aging, wrinkle treatment, skin resurfacing, etc. Each pulse of the laser diode bar generates one treatment zone corresponding to the collective beam from the multiple emitters.

| Parameter | Example values | Specific example |
|---|---|---|
| Laser diode bar | | |
| fill factor | 50%-90% | about 70% |
| number of emitters | 49-89 | 69 |
| emitter width $W_E$ | 90-150 μm | 100 μm |
| emitter spacing $W_S$ | 10-100 μm | 40 μm |
| Total optical efficiency (laser diode bar to target) | 70%-90% | about 80% |
| Proximity gap spacing | 1 mm-10 mm | about 1.5-2.5 mm |
| Power emitted | | |
| per emitter | 0.45-1.4 W | 0.9 W |
| total emitted by diode bar | 40-70 W | 60 W |
| Pulse characteristics | | |
| pulse on-time | 10-500 ms | 25 ms |
| duty cycle | 10-60% | 50% |
| Length of instantaneous irradiated area on target (perpendicular to elongated direction of diode bar) | 0.5-3 mm | 1 mm |
| Glide speed | 2-6 cm/s | 4 cm/s |
| Width of treatment zone (parallel to elongated direction of diode bar) | 1-2 cm | 1 cm |
| Length of treatment zone (perpendicular to elongated direction of diode bar) | 1-6 mm | 2 mm |
| Area of treatment zone | 0.1-1.2 cm$^2$ | 0.2 cm$^2$ |
| Energy delivered per treatment zone | 0.5-30 J | 1.2 J |
| Length of non-irradiated areas between successive treatment zones (perpendicular to elongated direction of diode bar) | 0.5-5 mm | 1 mm |

3. Direct exposure embodiment with low fill-factor laser diode bar, operating in a gliding mode in which the device is glided perpendicular to the elongated direction of the laser diode bar, with pulsed radiation for fractional treatment. Each pulse of the laser diode bar generates multiple separated-apart treatment zones, each corresponding to one of the emitters of the laser diode bar.

| Parameter | Example values | Specific example |
|---|---|---|
| Laser diode bar | | |
| fill factor | 10%-40% | about 30% |
| number of emitters | 9-39 | 29 |
| emitter width $W_E$ | 90-200 μm | 150 μm |
| emitter spacing $W_S$ | 150-900 μm | 350 μm |
| Total optical efficiency (laser diode bar to target) | 70%-90% | about 80% |
| Proximity gap spacing | 1 mm-10 mm | about 1.5-2.5 mm |
| Power emitted | | |
| per emitter | 1.3-9 W | 2.4 W |
| total emitted by diode bar | 50-80 W | 70 W |
| Pulse characteristics | | |
| pulse on-time | 2-20 ms | 6 ms |
| duty cycle | 10-60% | 50% |
| Length of instantaneous irradiated area on target from single emitter (perpendicular to elongated direction of diode bar) | 0.2-0.6 mm | 0.2 mm |
| Width of instantaneous irradiated area on target from single emitter (parallel to elongated direction of diode bar) | 0.2-0.6 mm | 0.3 mm |
| Glide speed | 2-6 cm/s | 4 cm/s |
| Total width of treatment zone pattern (parallel to elongated direction of diode bar) | 1-2 cm | 1 cm |
| Length of individual treatment zone (perpendicular to elongated direction of diode bar) | 0.2-1 mm | 0.3 mm |
| Area of individual treatment zone | 0.04-0.6 mm$^2$ | 0.09 mm$^2$ |
| Width of non-irradiated areas between individual treatment zones (parallel to elongated direction of diode bar) | 150-800 μm | 300 μm |
| Energy delivered per individual treatment zone | 2-150 mJ | 12 mJ |
| Length of non-irradiated areas between successive treatment zone patterns (perpendicular to elongated direction of diode bar) | 0.2-1.2 mm | 0.25 mm |

The particular embodiments disclosed herein are illustrative only, as the invention may be modified and practiced in different but equivalent manners apparent to those having ordinary skill in the art and having the benefit of the teachings herein. While numerous changes may be made by those having ordinary skill in the art, such changes are encompassed within the spirit and scope of this invention as defined by the appended claims. Furthermore, no limitations are intended to the details of construction or design herein shown. It is therefore evident that the particular illustrative embodiments disclosed above may be altered or modified and all such variations are considered within the scope and spirit of the present invention.

The invention claimed is:

1. A dermatological treatment device, comprising:
   a device body having an application end including a skin-contacting surface configured to be placed in contact with a skin surface during treatment;
   a laser diode bar having multiple emitters configured to generate laser radiation for delivery to the skin surface, the laser diode bar having a fill factor of at least 50%;
   a power source;
   control electronics configured to provide power from the power source to the laser diode bar such that each emitter of the laser diode bar generates and emits a discrete laser beamlet;
   wherein the device includes no optics downstream of the laser diode bar; and
   wherein the laser diode bar is arranged with respect to the application end of the device body such that with the application end of the device body arranged in contact with the skin surface, the discrete beamlets emitted by the multiple emitters combine before reaching an output plane defined by the skin-contacting surface of the device to form a collective beam at the output plane that provides a contiguous treatment zone at the skin surface for a dermatological treatment.

2. The dermatological treatment device according to claim 1, wherein the laser diode bar has a fill factor of at least 75%.

3. The dermatological treatment device according to claim 1, wherein the laser diode bar is arranged such that an emitting surface of the laser diode bar is spaced from the output plane defined by the skin-contacting surface of the device by less than 5 mm.

4. The dermatological treatment device according to claim 1, wherein the laser diode bar emits radiation at a wavelength of between 650 nm and 1100 nm.

5. The dermatological treatment device according to claim 4, wherein the laser diode bar emits radiation at a wavelength of approximately 810 nm.

6. The dermatological treatment device according to claim 1, wherein the laser diode bar emits radiation at a wavelength of between 1400 nm and 2000 nm.

7. The dermatological treatment device according to claim 1, wherein the control electronics comprise:
a processor; and
computer instructions stored in a non-transitory computer-readable medium and executable by the processor to control the laser diode bar to generate continuous wave (CW) radiation during movement of the application end across the surface of the skin, such that a continuous treatment zone is formed in the direction of the device movement across the skin.

8. The dermatological treatment device according to claim 1, wherein the control electronics comprise:
a processor; and
computer instructions stored in a non-transitory computer-readable medium and executable by the processor sequentially deliver a series of collective beams to the skin to generate treatment zones on the skin spaced apart from each other by areas of non-irradiated skin between the adjacent treatment zones, to provide a fractional treatment to the skin.

9. The dermatological treatment device according to claim 1, wherein the control electronics comprise:
a processor; and
computer instructions stored in a non-transitory computer-readable medium and executable by the processor to pulse the laser diode bar to sequentially deliver a series of collective beams to the skin to generate treatment zones on the skin during movement of the application end across the surface of the skin, such that adjacent treatment zones generated on the skin are spaced apart from each other by areas of non-treated skin between the adjacent treatment zones.

10. The dermatological treatment device according to claim 1, wherein the collective beam is divergent in the at least one direction upon incidence with the skin surface.

11. The dermatological treatment device according to claim 1, wherein the contiguous treatment zone defines an uniform line segment.

12. The dermatological treatment device according to claim 1, wherein the skin-contacting surface comprises a surface of a bezel having an opening through which the collective beam passes.

13. The dermatological treatment device according to claim 12, wherein a window is arranged in the opening of the bezel.

14. The dermatological treatment device according to claim 1, wherein the skin-contacting surface comprises a surface of a window arranged downstream of the laser diode bar.

15. A dermatological treatment device, comprising:
a device body having an application end configured to be placed in contact with a skin surface;
a laser diode bar having multiple emitters configured to generate laser radiation for delivery to the skin surface;
a power source and control electronics configured to provide power to the laser diode bar such that the each emitter of the laser diode bar simultaneously generates and emits a discrete laser beamlet;
wherein the device includes no optics downstream of the laser diode bar, and
wherein the laser diode bar is arranged with respect to the application end of the device body such that with the application end of the device body arranged in contact with the skin surface, the discrete beamlets simultaneously emitted by the multiple emitters combine before reaching the skin surface to form an instantaneous collective beam that provides an instantaneous contiguous treatment zone at the skin surface for a dermatological treatment.

16. The dermatological treatment device according to claim 15, wherein the laser diode bar has a fill factor of at least 50%.

17. The dermatological treatment device according to claim 15, wherein: the application end of the device body is configured to be in contact with the skin during delivery of the laser radiation; and the laser diode bar is arranged such that when the application end is in contact with the skin, an emitting surface of the laser diode bar is spaced from the skin surface by less than 5 mm.

18. The dermatological treatment device according to claim 15, wherein the device is fully solid-state with no automated moving components.

19. The dermatological treatment device according to claim 15, wherein the collective beam is divergent in the at least one direction upon incidence with the skin surface.

20. The dermatological treatment device according to claim 15, wherein the contiguous treatment zone defines a uniform line segment.

21. The dermatological treatment device according to claim 20, wherein the laser diode bar has a fill factor of at least 75%.

22. The dermatological treatment device according to claim 20, wherein the laser diode bar is arranged such that an emitting surface of the laser diode bar is spaced from the output plane defined by the skin-contacting surface of the device by less than 5 mm.

23. The dermatological treatment device according to claim 20, wherein the control electronics comprise:
a processor; and
computer instructions stored in a non-transitory computer-readable medium and executable by the processor to control the laser diode bar to generate continuous wave (CW) radiation during movement of the application end across the surface of the skin, such that a continuous treatment zone is formed in the direction of the device movement across the skin.

24. The dermatological treatment device according to claim 20, wherein the control electronics comprise:
a processor; and
computer instructions stored in a non-transitory computer-readable medium and executable by the processor sequentially deliver a series of collective beams to the skin to generate treatment zones on the skin spaced apart from each other by areas of non-irradiated skin between the adjacent treatment zones, to provide a fractional treatment to the skin.

25. The dermatological treatment device according to claim 20, wherein the control electronics comprise:
a processor; and
computer instructions stored in a non-transitory computer-readable medium and executable by the processor to pulse the laser diode bar to sequentially deliver a series of collective beams to the skin to generate treatment zones on the skin during movement of the application end across the surface of the skin, such that adjacent treatment zones generated on the skin are spaced apart from each other by areas of non-treated skin between the adjacent treatment zones.

26. The dermatological treatment device according to claim 20, wherein the collective beam is divergent in the at least one direction upon incidence with the skin surface.

27. The dermatological treatment device according to claim 20, wherein the contiguous treatment zone defines a uniform line segment.

28. A dermatological treatment device, comprising:
a device body having an application end including a skin-contacting surface configured to be placed in contact with a skin surface;
a laser diode bar having multiple emitters configured to generate laser radiation for delivery to the skin surface via the application end of the device body;
a power source and control electronics configured to provide power to the laser diode bar such that each emitter of the laser diode bar generates and emits a discrete laser beamlet;
wherein the laser diode bar is arranged with respect to the application end of the device body such that with the application end of the device body arranged in contact with the skin surface, (a) an emitting surface of the laser diode bar is spaced from the skin surface by less than 5 mm, and (b) the discrete beamlets emitted by the multiple emitters combine before reaching an output plane defined by the skin-contacting surface of the device to form a collective beam at the output plane that defines a contiguous irradiated area at the skin surface for a dermatological treatment;
wherein the application end is configured to be moved across the skin surface during delivery of the collective beam to the skin surface to form a contiguous treatment zone defined by a travel of the contiguous irradiated area due to the movement of the application end across the skin.

29. The dermatological treatment device according to claim 28, wherein the control electronics comprise:
a processor; and
computer instructions stored in a non-transitory computer-readable medium and executable by the processor to control the laser diode bar to generate continuous wave (CW) radiation during movement of the application end across the surface of the skin, such that a single contiguous treatment zone is formed in the direction of the device movement across the skin.

30. The dermatological treatment device according to claim 28, wherein the control electronics comprise:
a processor; and
computer instructions stored in a non-transitory computer-readable medium and executable by the processor to pulse the laser diode bar to sequentially deliver a series of collective beams to the skin to generate a series of contiguous treatment zones on the skin the during movement of the application end across the surface of the skin, such that adjacent contiguous treatment zones generated on the skin are spaced apart from each other by areas of non-treated skin between the adjacent contiguous treatment zones.

31. The dermatological treatment device according to claim 28, wherein the laser diode bar has a fill factor of at least 50%.

32. The dermatological treatment device according to claim 28, further comprising a diffuser downstream of the laser diode bar.

33. The dermatological treatment device according to claim 32, further comprising a window downstream of the diffuser.

34. The dermatological treatment device according to claim 28, wherein the contiguous irradiated area defines a uniform line segment.

35. A dermatological treatment device, comprising:
a device body having an application end including a skin-contacting surface configured to be placed in contact with a skin surface during treatment;
a laser diode bar having multiple emitters configured to generate laser radiation for delivery to the skin surface, the laser diode bar having a fill factor of at least 50%;
a power source;
control electronics configured to provide power from the power source to the laser diode bar such that each emitter of the laser diode bar generates and emits a discrete laser beamlet;
wherein the device includes, downstream of the laser diode bar, only an open air interface, a window, or other structure that does not deflect or influence the angular distribution profile of the emitted laser beamlets; and
wherein the laser diode bar is arranged with respect to the application end of the device body such that with the application end of the device body arranged in contact with the skin surface, the discrete beamlets emitted by the multiple emitters combine before reaching an output plane defined by the skin-contacting surface of the device to form a collective beam at the output plane that provides a contiguous treatment zone at the skin surface to provide a dermatological treatment.

36. The dermatological treatment device according to claim 28, wherein the skin-contacting surface comprises a surface of a bezel having an opening through which the collective beam passes.

37. The dermatological treatment device according to claim 36, wherein a window is arranged in the opening of the bezel.

38. The dermatological treatment device according to claim 28, wherein the skin-contacting surface comprises a surface of a window arranged downstream of the laser diode bar.

39. A dermatological treatment device, comprising:
a device body having an application end configured to be placed in contact with a skin surface;
a laser diode bar having multiple emitters configured to generate laser radiation for delivery to the skin surface;
a power source and control electronics configured to provide power to the laser diode bar such that the each emitter of the laser diode bar simultaneously generates and emits a discrete laser beamlet;
wherein the device includes, downstream of the laser diode bar, only an open air interface, a window, or other structure that does not deflect or influence the angular distribution profile of the emitted laser beamlets; and
wherein the laser diode bar is arranged with respect to the application end of the device body such that with the application end of the device body arranged in contact with the skin surface, the discrete beamlets simultaneously emitted by the multiple emitters combine before reaching the skin surface to form an instantaneous collective beam that provides an instantaneous contiguous treatment zone at the skin surface for a dermatological treatment.

40. The dermatological treatment device according to claim 39, wherein the laser diode bar has a fill factor of at least 50%.

41. The dermatological treatment device according to claim 39, wherein the laser diode bar has a fill factor of at least 75%.

42. The dermatological treatment device according to claim 39, wherein: the application end of the device body is configured to be in contact with the skin during delivery of the laser radiation; and the laser diode bar is arranged such that when the application end is in contact with the skin, an emitting surface of the laser diode bar is spaced from the skin surface by less than 5 mm.

43. The dermatological treatment device according to claim 39, wherein the control electronics comprise:
   a processor; and
   computer instructions stored in a non-transitory computer-readable medium and executable by the processor to control the laser diode bar to generate continuous wave (CW) radiation during movement of the application end across the surface of the skin, such that a continuous treatment zone is formed in the direction of the device movement across the skin.

44. The dermatological treatment device according to claim 39, wherein the control electronics comprise:
   a processor; and
   computer instructions stored in a non-transitory computer-readable medium and executable by the processor sequentially deliver a series of collective beams to the skin to generate treatment zones on the skin spaced apart from each other by areas of non-irradiated skin between the adjacent treatment zones, to provide a fractional treatment to the skin.

45. The dermatological treatment device according to claim 39, wherein the control electronics comprise:
   a processor; and
   computer instructions stored in a non-transitory computer-readable medium and executable by the processor to pulse the laser diode bar to sequentially deliver a series of collective beams to the skin to generate treatment zones on the skin during movement of the application end across the surface of the skin, such that adjacent treatment zones generated on the skin are spaced apart from each other by areas of non-treated skin between the adjacent treatment zones.

46. The dermatological treatment device according to claim 39, wherein the collective beam is divergent in the at least one direction upon incidence with the skin surface.

47. The dermatological treatment device according to claim 39, wherein the contiguous treatment zone defines a uniform line segment.

* * * * *